US012751716B2

(12) United States Patent

Nakamura et al.

(10) Patent No.: US 12,751,716 B2

(45) Date of Patent: Oct. 6, 2026

(54) MEDICAL STAPLER AND SUTURING METHOD

(71) Applicant: OLYMPUS CORPORATION, Tokyo (JP)

(72) Inventors: Takashi Nakamura, Saitama (JP); Keita Ozawa, Hino (JP); Chisato Karasawa, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 270 days.

(21) Appl. No.: 18/595,874

(22) Filed: Mar. 5, 2024

(65) Prior Publication Data

US 2024/0206878 A1 Jun. 27, 2024

Related U.S. Application Data

(63) Continuation of application No. PCT/JP2021/033267, filed on Sep. 10, 2021.

(51) Int. Cl.

| | |
|---|---|
| ***A61B 17/115*** | (2006.01) |
| ***A61B 1/00*** | (2006.01) |
| ***A61B 17/00*** | (2006.01) |
| ***A61B 17/072*** | (2006.01) |
| ***A61B 17/29*** | (2006.01) |

(52) U.S. Cl.

CPC ........ *A61B 17/115* (2013.01); *A61B 1/00195* (2013.01); *A61B 2017/00818* (2013.01); *A61B 2017/07257* (2013.01); *A61B 17/29* (2013.01)

(58) Field of Classification Search

CPC ... A61B 17/115; A61B 1/00195; A61B 17/29; A61B 2017/00818; A61B 2017/07257; A61B 17/00234; A61B 17/0469; A61B 2017/00296; A61B 2017/2905;

(Continued)

(56) References Cited

U.S. PATENT DOCUMENTS

2004/0138682 A1 7/2004 Onuki et al.
2018/0042603 A1 2/2018 Mitelberg et al.

(Continued)

FOREIGN PATENT DOCUMENTS

JP 11506943 A 6/1999
JP 2000166936 A 6/2000

(Continued)

OTHER PUBLICATIONS

"International Application Serial No. PCT/JP2021/033267, International Search Report dated Dec. 7, 2021", w/ English Translation, (Dec. 7, 2021), 4 pgs.

*Primary Examiner* — Veronica Martin

(74) *Attorney, Agent, or Firm* — Schwegman Lundberg & Woessner, P.A.

(57) ABSTRACT

A medical stapler includes a stapling head having a staple ejection portion and having a length in one direction, an anvil openably and closably coupled to the stapling head by a rotation shaft and having a length in one direction, a staple receiving portion provided in the anvil and provided at a position facing the staple ejection portion when the stapling head and the anvil are in a closed state, and a first guide portion configured to be displaced to a protruding orientation or a retracted orientation. In the protruding orientation, the first guide portion is capable of lifting a treatment tool.

17 Claims, 26 Drawing Sheets

(58) Field of Classification Search
CPC .......... A61B 1/018; A61B 2017/00269; A61B 17/0218; A61B 10/06
See application file for complete search history.

(56) References Cited

U.S. PATENT DOCUMENTS

| | | | | |
|---|---|---|---|---|
| 2020/0275925 | A1* | 9/2020 | Smith .................... | A61B 1/018 |
| 2021/0022733 | A1 | 1/2021 | Smith et al. | |

FOREIGN PATENT DOCUMENTS

| | | | |
|---|---|---|---|
| JP | 2004041733 | A | 2/2004 |
| JP | 2004503325 | A | 2/2004 |
| WO | WO-9618344 | A2 | 6/1996 |
| WO | WO-0205721 | A2 | 1/2002 |

* cited by examiner

MEDICAL STAPLER AND SUTURING METHOD

TECHNICAL FIELD

The present disclosure relates to a medical stapler and a suturing method.

This application is a continuation application of PCT International Application No. PCT/JP2021/033267, filed on Sep. 10, 2021. The content of the above-identified PCT International Applications is incorporated herein by reference.

BACKGROUND ART

In recent years, a medical stapler such as a stapler has been used in a surgery for suturing the digestive tract or the like. When an appropriate medical stapler is used, the surgery for suturing the digestive tract or the like can be made easier and a surgical time can be significantly reduced.

As a conventional medical stapler, for example, there is one including an endoscope and a stapling mechanism disposed around the endoscope disclosed in United States Patent Application, Publication No. 2018/0042603 (hereinafter, referred to as Patent Document). In the configuration of the Patent Document, a suturing treatment on a treatment target can be performed by the stapling mechanism while observing the treatment target using the endoscope.

However, when the medical stapler described in the Patent Document is used to suture a treatment target using the stapling mechanism, it has been difficult to ascertain a suture position and whether or not suturing can be performed in a state in which a diseased tissue is fully included.

In view showing the above circumstances, an objective of the present disclosure is to provide a medical stapler and a suturing method capable of causing a suture position to be easily ascertained and improving a treatment effect.

SUMMARY

In order to solve the above problems, the present disclosure proposes the following aspects.

A medical stapler according to a first aspect of the present disclosure includes a stapling head including a staple ejection portion and having a length in one direction, an anvil openably and closably coupled to the stapling head by a rotation shaft and having a length in one direction, a staple receiving portion provided in the anvil and provided at a position facing the staple ejection portion when the stapling head and the anvil are in a closed state, and a first guide portion configured to be displaced to a protruding orientation or a retracted orientation. In the protruding orientation, the first guide portion protrudes in a direction in which the anvil opens with respect to the stapling head when the anvil is in a closed state with respect to the stapling head. In the retracted orientation, the first guide portion does not protrude in the direction in which the anvil opens with respect to the stapling head when the anvil is in an open state with respect to the stapling head. In the protruding orientation, the first guide portion is capable of lifting a treatment tool.

A suturing method according to a second aspect of the present disclosure includes an insertion step of inserting a medical stapler and an endoscope into the body, a first advancing step of advancing a treatment tool from a distal-end portion of the endoscope, a grasping step of grasping a treatment target inside the body with the treatment tool, a retracting step of retracting the treatment tool relative to the medical stapler to draw in a tissue containing the treatment target to an endoscope side through a visual space of the medical stapler, an observation step of projecting the treatment target within a field of view showing the endoscope, and a suturing step of ejecting a staple from the stapling head to suture a circumference of the treatment target.

Advantageous Effects of Invention

The medical stapler and suturing method of the present disclosure can cause a suture position to be easily ascertained and improve a treatment effect.

DESCRIPTION OF EMBODIMENTS

First Embodiment

A first embodiment of the present disclosure will be described with reference to FIGS. 1 to 18.

Figure 1:
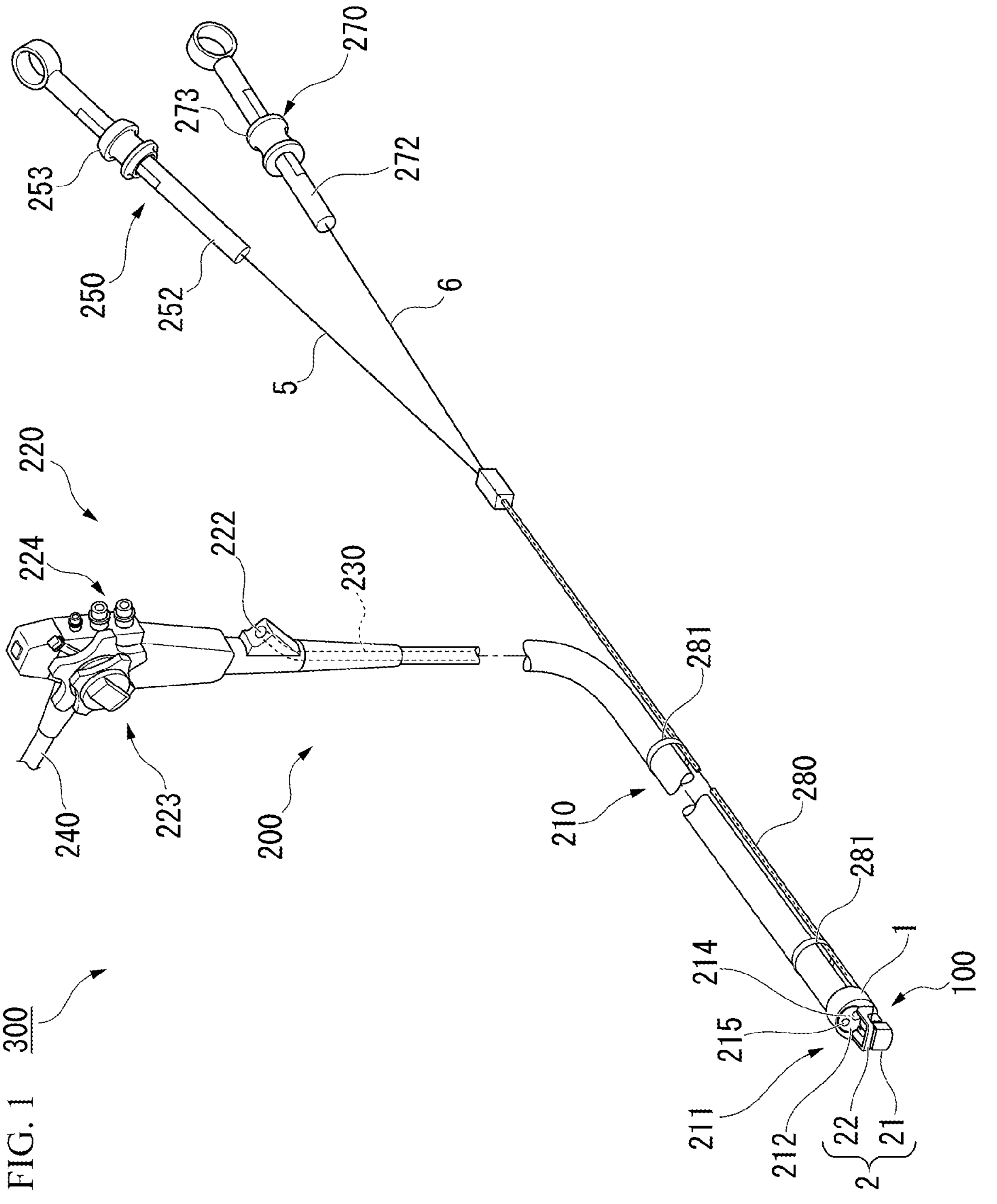
FIG. 1 is a view showing an overall configuration of a medical system including a medical stapler according to a first embodiment.

FIG. 1 is a view showing an overall configuration of a medical system 300 including a medical stapler 100 according to the present embodiment.

Medical System 300

The medical system 300 is used for a surgery or the like in which the digestive tract or the like is sutured. The medical system 300 includes the medical stapler 100, an endoscope 200, an open-close operation unit 250, an ejection operation unit 270, and a wire sheath 280. The open-close operation unit 250 is an operation unit that operates the medical stapler 100 using an open-close operation wire 5. The ejection operation unit 270 is an operation unit that operates the medical stapler 100 using an ejection operation wire 6.

Endoscope 200

The endoscope 200 is a known flexible endoscope, and includes a long insertion portion 210 that is inserted into the body from a distal end thereof, an operation unit 220 provided at a proximal-end portion of the insertion portion 210, and a universal cord 240.

A treatment tool channel 230 through which an endoscopic treatment tool is inserted is formed in the insertion portion 210. A forceps port 214, which is a distal end opening of the treatment tool channel 230, is provided at a distal end 212 of the insertion portion 210. The treatment tool channel 230 extends from the distal end 212 of the insertion portion 210 to the operation unit 220.

A distal-end portion 211 of the insertion portion 210 includes an imaging unit (not shown in the drawings) including a CCD or the like. An objective lens 215 of the imaging unit is exposed at the distal end 212 of the insertion portion 210.

A knob 223 that operates the insertion portion 210 and a switch 224 that operates the imaging unit or the like are provided on a proximal-end side of the operation unit 220. An operator can bend the insertion portion 210 in a desired direction by operating the knob 223.

A forceps insertion port 222 communicating with the treatment tool channel 230 is provided on a distal-end side of the operation unit 220. The operator can insert the endoscopic treatment tool into the treatment tool channel 230 through the forceps insertion port 222.

The universal cord 240 connects the operation unit 220 and an external peripheral device. The universal cord 240 outputs, for example, an image captured by the imaging unit to an external device. The image captured by the imaging unit is displayed on a display device such as a liquid crystal display via an image processing device.

Open-Close Operation Unit 250

The open-close operation unit 250 is an operation unit that opens and closes the medical stapler 100 by operating the open-close operation wire 5. As shown in FIG. 1, the open-close operation unit 250 includes an open-close operation unit main body 252 and an open-close operation slider 253. A proximal end of the open-close operation wire 5 is coupled to the open-close operation slider 253. The operator can advance and retract the open-close operation wire 5 by advancing and retracting the open-close operation slider 253 in a longitudinal axis direction with respect to the open-close operation unit main body 252.

Ejection Operation Unit 270

The ejection operation unit 270 is an operation unit that ejects a staple S (FIG. 10) from the medical stapler 100 by operating the ejection operation wire 6. As shown in FIG. 1, the ejection operation unit 270 includes an ejection operation unit main body 272 and an ejection operation slider 273. A proximal end of the ejection operation wire 6 is coupled to the ejection operation slider 273. The operator can advance and retract the ejection operation wire 6 by advancing and retracting the ejection operation slider 273 in a longitudinal axis direction with respect to the ejection operation unit main body 272.

Wire Sheath 280

The wire sheath 280 is a sheath through which the open-close operation wire 5 and the ejection operation wire 6 are inserted. As shown in FIG. 1, a distal-end side of the wire sheath 280 is coupled to the insertion portion 210 of the endoscope 200 by a plurality of bands 281.

Medical Stapler 100

Figure 2:
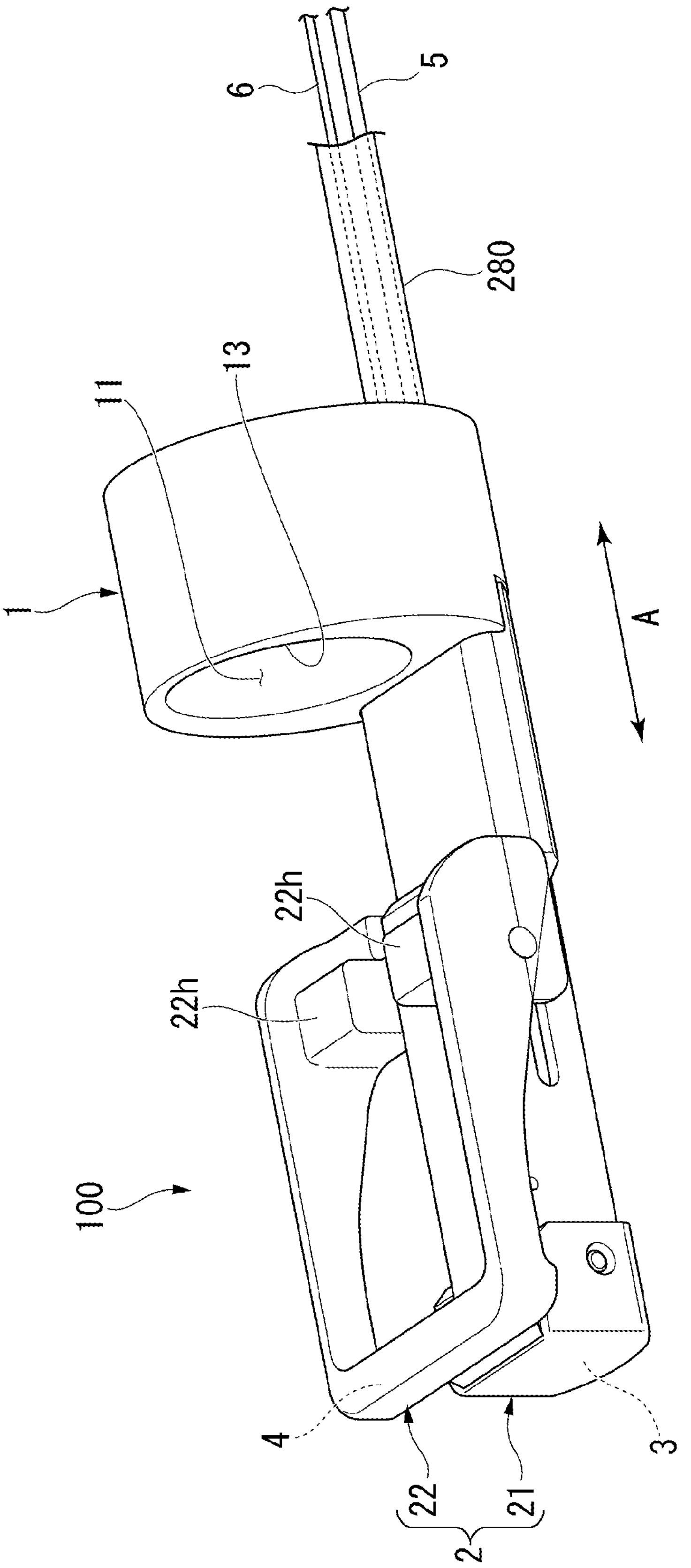
FIG. 2 is a perspective view showing the medical stapler according to the first embodiment.

FIG. 2 is a perspective view showing the medical stapler 100.

The medical stapler 100 includes a cap (attachment member) 1, a grasping portion 2, a staple ejection portion 3, a staple receiving portion 4, an open-close operation wire 5, and an ejection operation wire (power transmission member) 6. The medical stapler 100 is attachable to and detachable from the distal-end portion 211 of the insertion portion 210 shown in FIG. 1.

Figure 3:
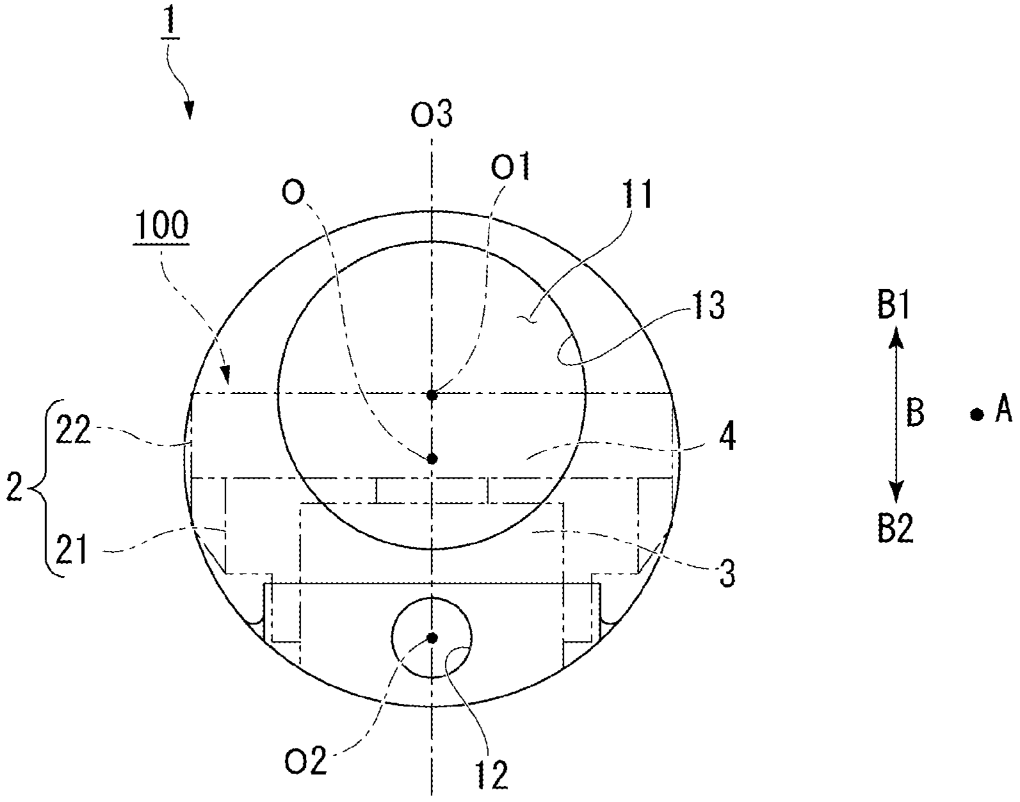
FIG. 3 is a front view showing a cap of the medical stapler.

FIG. 3 is a front view showing the cap 1. In FIG. 3, the grasping portion 2 is displayed by a two-dotted line.

The cap (attachment member) 1 is a member that is attachable to the distal-end portion 211 of the endoscope 200. The cap 1 is formed in a substantially columnar shape and has a first through hole 11 penetrating in an axial direction A (FIG. 2) and a second through hole 12 penetrating in the axial direction A.

The first through hole 11 is a hole into which the distal-end portion 211 of the insertion portion 210 shown in FIG. 1 is inserted. A shape of the first through hole 11 is formed to follow an outer shape of the distal-end portion 211 of the insertion portion 210. Therefore, when the distal-end portion 211 of the endoscope 200 is inserted into the first through hole 11, the cap 1 can be attached to the distal-end portion 211 of the endoscope 200.

A central axis O1 of the first through hole 11 in the axial direction A is eccentric with respect to a central axis O of the cap 1 in the axial direction A. A direction in which the central axis O1 is eccentric with respect to the central axis O is defined as an "upward side B1".

The second through hole 12 is a hole into which the wire sheath 280, through which the open-close operation wire 5 and the ejection operation wire 6 shown in FIG. 1 are inserted, is inserted. An inner diameter of the second through hole 12 is substantially coincident with an outer diameter of the wire sheath 280.

A distal-end portion of the wire sheath 280 is inserted through the second through hole 12 to be fixed. The open-close operation wire 5 and the ejection operation wire 6 which are inserted through the wire sheath 280 pass through the second through hole 12 and extend to a distal-end side thereof.

The central axis O2 of the second through hole 12 in the axial direction A is eccentric with respect to the central axis O of the cap 1 in the axial direction A as shown in FIG. 3. A direction in which the central axis O2 is eccentric with respect to the central axis O is opposite to the direction (the upward side B1) in which the central axis O1 is eccentric with respect to the central axis O. A direction in which the central axis O2 is eccentric with respect to the central axis O is defined as a "downward side B2". In the present embodiment, the upward side B1 and the downward side B2 are directions extending in a vertical direction B.

Figure 4:
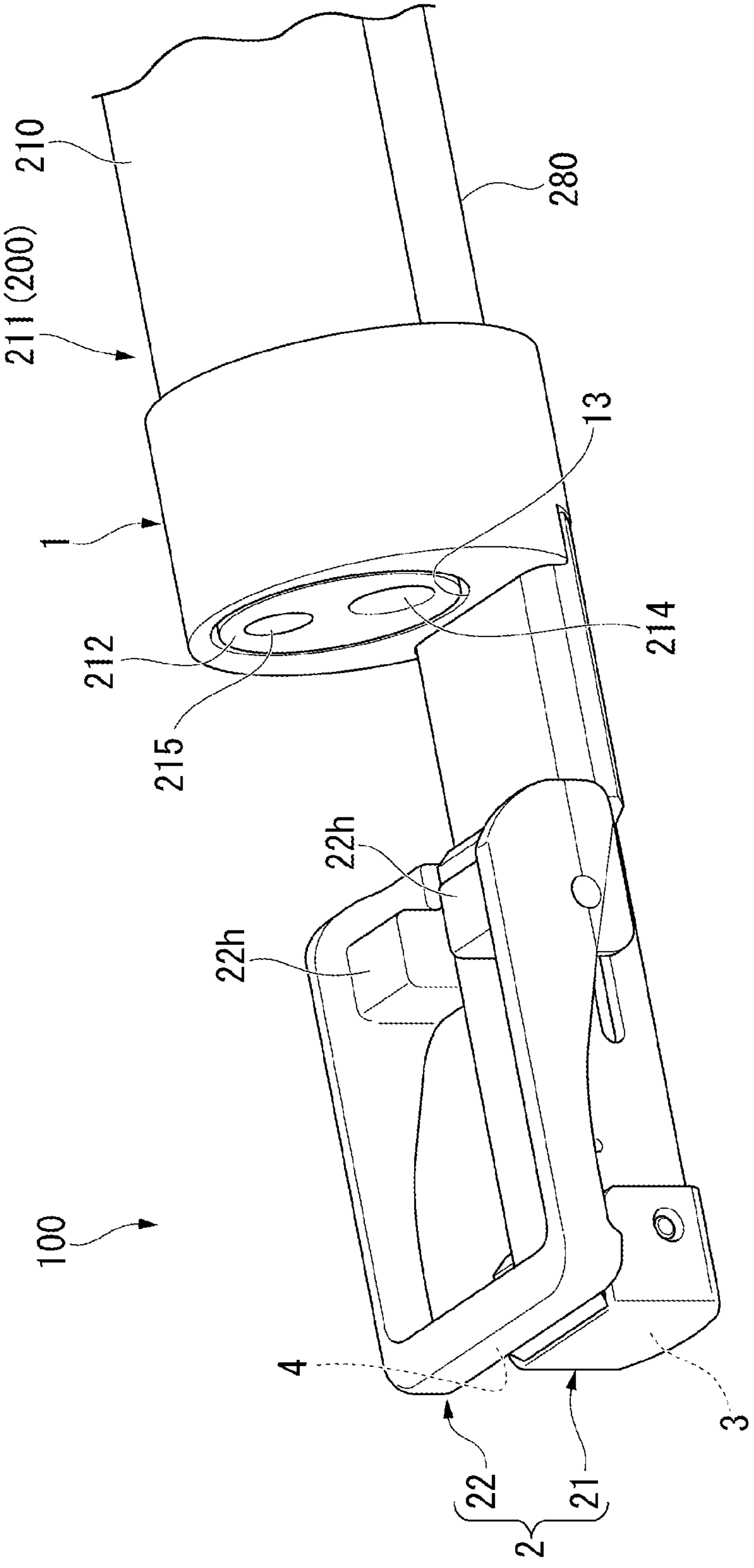
FIG. 4 is a perspective view showing the medical stapler with a grasping portion in a closed state.
Figure 5:
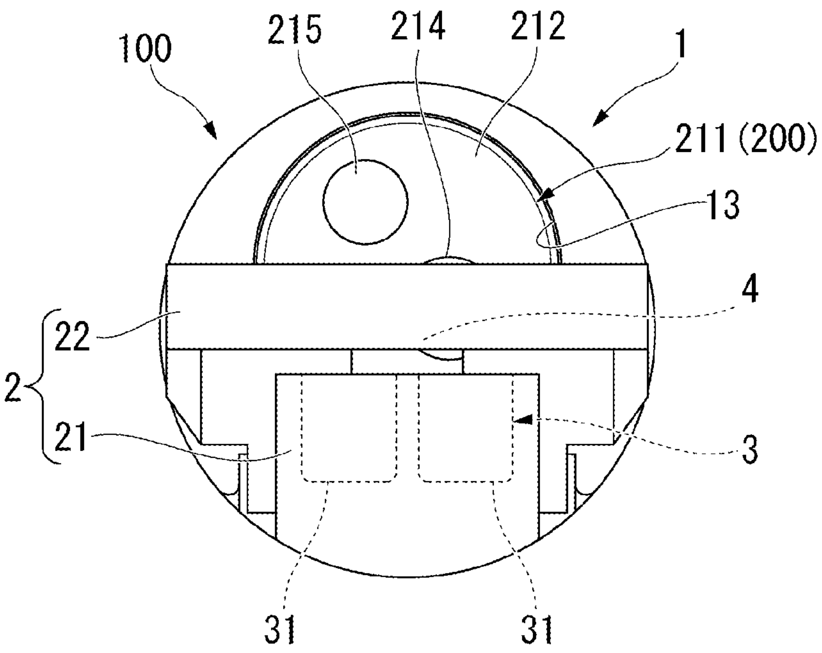
FIG. 5 is a front view showing the medical stapler with the grasping portion in a closed state.

FIG. 4 is a perspective view showing the medical stapler 100 with the grasping portion 2 in a closed state. FIG. 5 is a front view showing the medical stapler 100 with the grasping portion 2 in a closed state.

When the cap 1 is attached to the distal-end portion 211 of the endoscope 200, as shown in FIGS. 4 and 5, the objective lens 215 and the forceps port 214 are exposed from an opening 13 on a distal-end side of the first through hole 11 of the cap 1. The operator can observe a treatment target through the objective lens 215 even when the medical stapler 100 is attached to the distal-end portion 211 of the endoscope 200.

Figure 6:
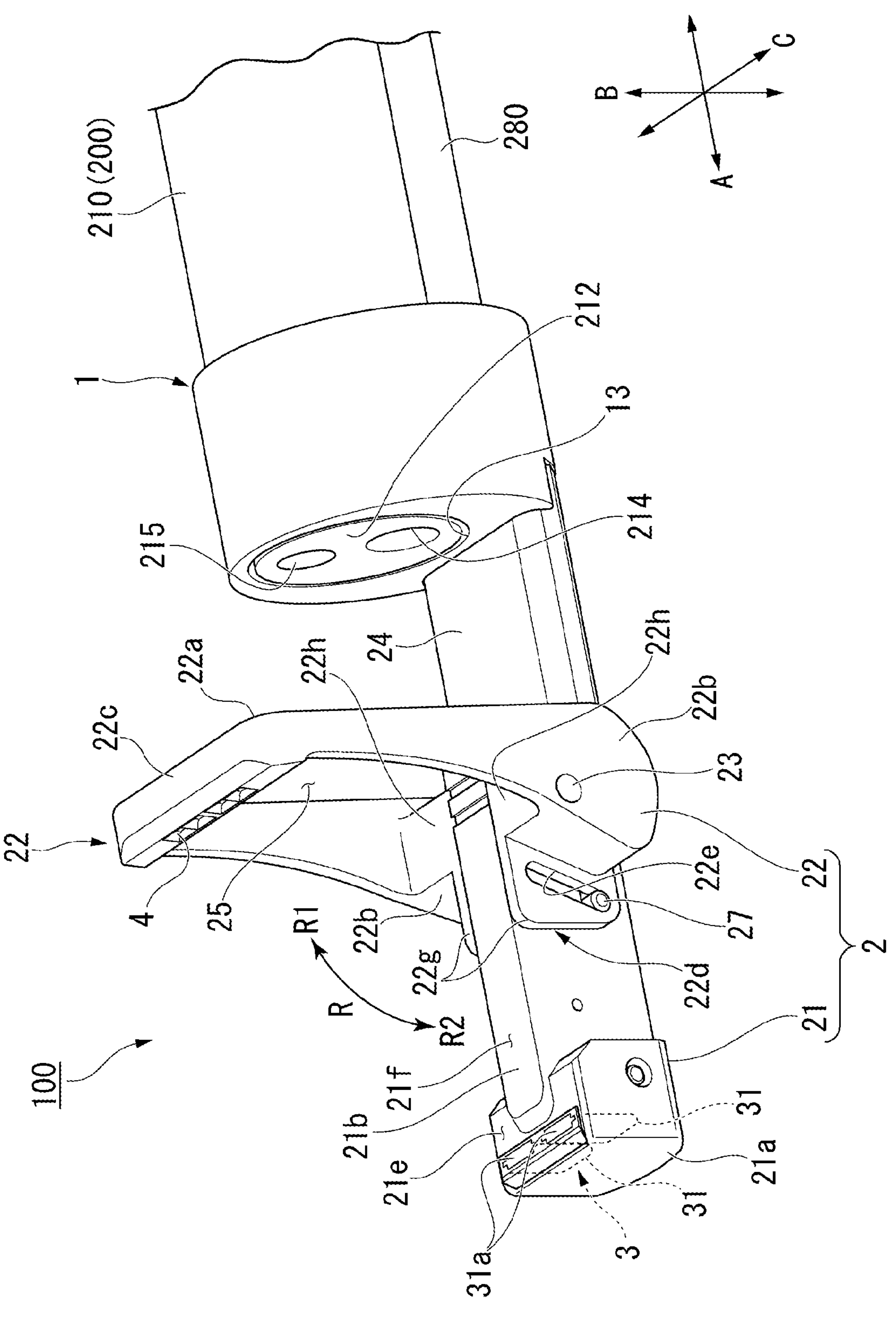
FIG. 6 is a perspective view showing the medical stapler with the grasping portion in an open state.
Figure 7:
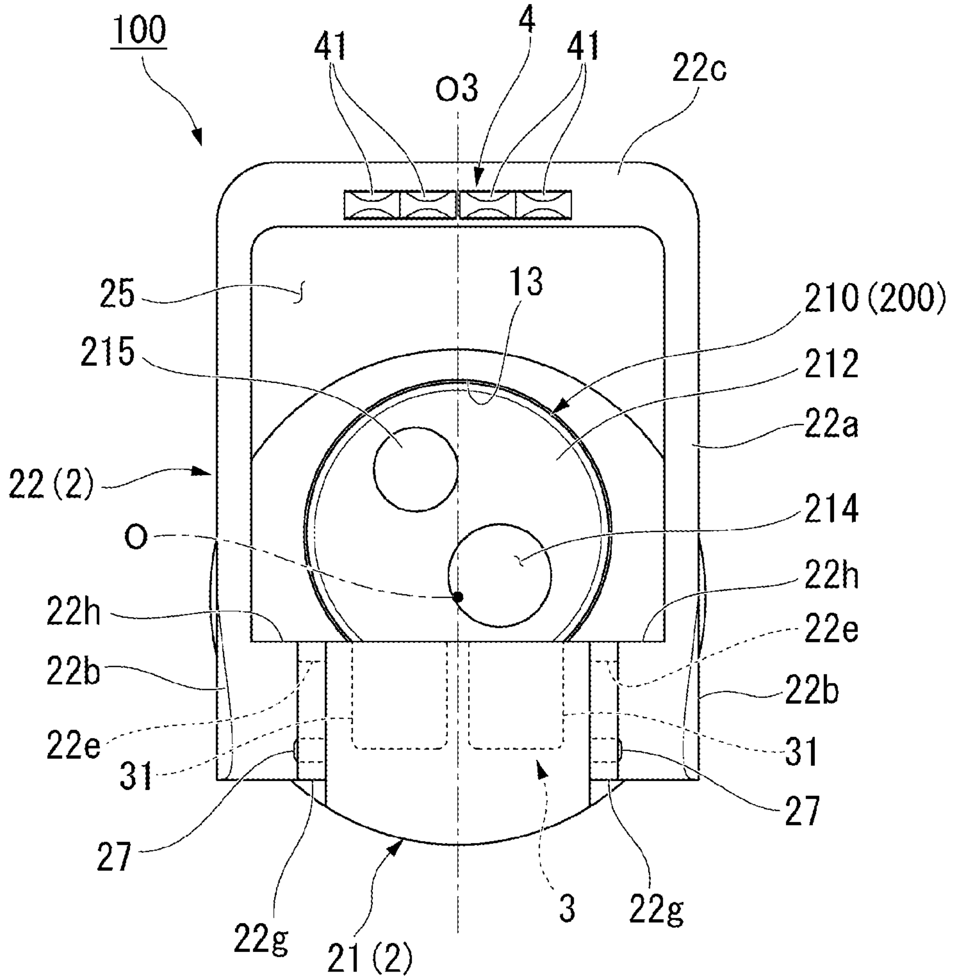
FIG. 7 is a front view showing the medical stapler with the grasping portion in an open state.
Figure 8:
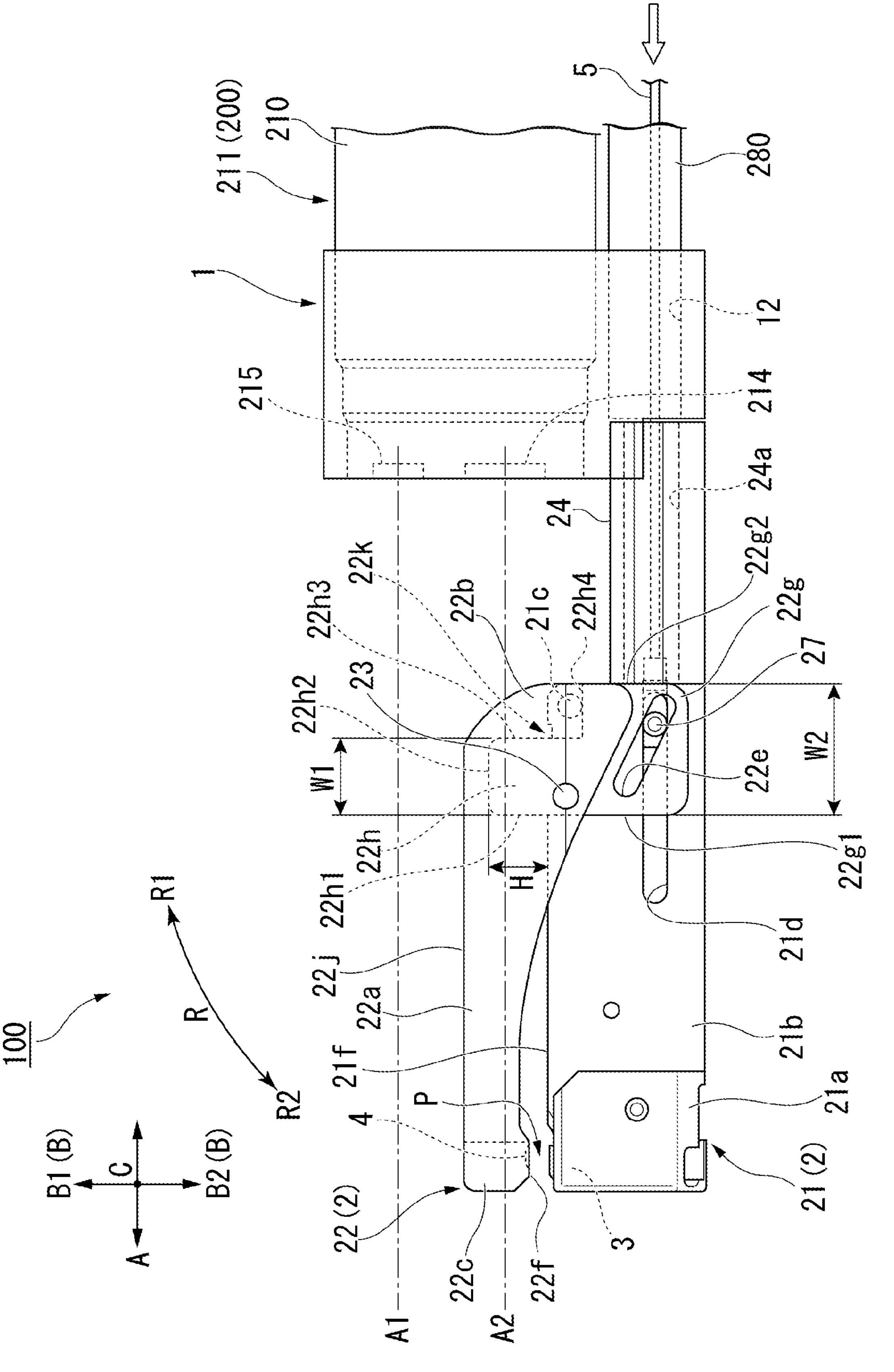
FIG. 8 is a side view showing the medical stapler with the grasping portion in a closed state.
Figure 9:
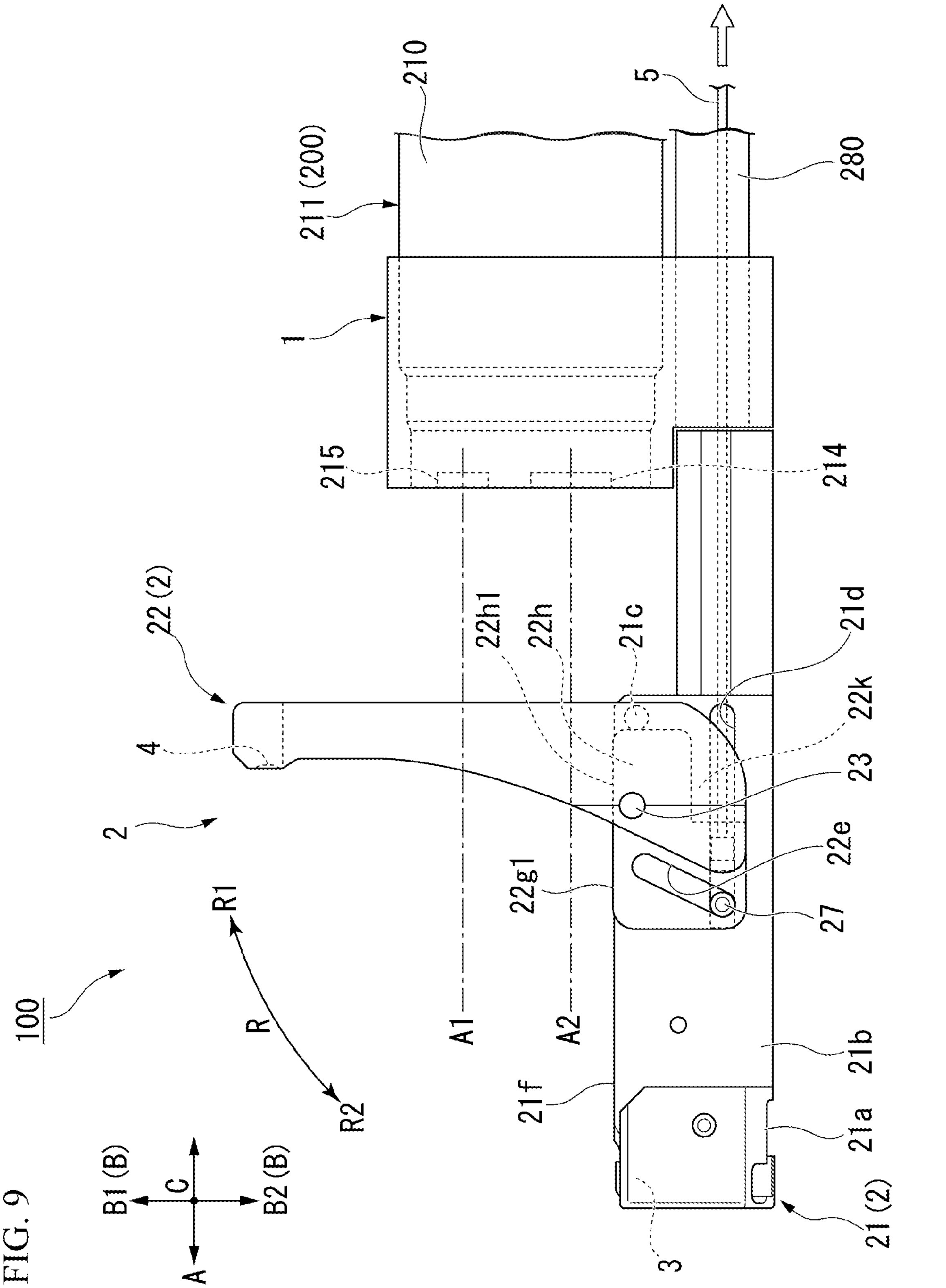
FIG. 9 is a side view showing the medical stapler with the grasping portion in an open state.

FIG. 6 is a perspective view showing the medical stapler 100 with the grasping portion 2 in an open state. FIG. 7 is a front view showing the medical stapler 100 with the grasping portion 2 in an open state. Further, FIG. 8 is a side view showing the medical stapler 100 with the grasping portion 2 in a closed state. FIG. 9 is a side view showing the medical stapler 100 with the grasping portion 2 in an open state.

As shown in FIG. 6, the grasping portion 2 includes a stapling head (first grasping member) 21, an anvil (second grasping member) 22, an open-close rotation shaft 23, a movable pin 27, and an extended portion 24.

As shown in FIG. 6, the stapling head 21 and the anvil 22 are coupled to be openable and closable by the open-close rotation shaft 23. The open-close rotation shaft 23 is provided on the distal-end side with respect to the cap 1. An axial direction C of the open-close rotation shaft 23 is perpendicular to the axial direction A and the vertical direction B of the cap 1. As shown in FIG. 7, the grasping portion 2 is symmetrically formed with respect to the central axis O3 in the vertical direction B.

The stapling head 21 is non-rotatably fixed to the distal-end side of the cap 1. The stapling head 21 is fixed to the cap 1 at a position on the downward side B2 with respect to the central axis O of the cap 1. As shown in FIG. 3, the stapling head 21 is disposed at a position overlapping the second through hole 12 of the cap 1 in a front view. On the other hand, as shown in FIG. 7, the stapling head 21 is disposed at a position not overlapping the objective lens 215 and the forceps port 214 of the endoscope 200 in a front view.

As shown in FIG. 6, the stapling head 21 includes a first distal-end portion 21*a* and a first main body portion 21*b*, and is formed in a substantially T shape in a plan view. The first distal-end portion 21*a* is disposed on the distal-end side with respect to the first main body portion 21*b*.

The first distal-end portion 21*a* is formed in a substantially rectangular parallelepiped shape. The first distal-end portion 21*a* is formed in a rectangular shape extending in the axial direction C of the open-close rotation shaft 23 in a plan view. The staple ejection portion 3 is provided at the first distal-end portion 21*a*. An opening 31*a* of the staple ejection portion 3 is provided on a surface (upper surface 21*e*) of the first distal-end portion 21*a* on the upward side B1.

The first main body portion 21*b* is an elongated member extending in the axial direction A. A distal end of the first main body portion 21*b* is fixed to the first distal-end portion 21*a*. A proximal end of the first main body portion 21*b* is fixed to the cap 1 via the extended portion 24.

In the present embodiment, the extended portion 24 for securing a distance from the endoscope 200 is provided on a proximal-end side of the grasping portion 2, but the present embodiment is not limited to this configuration. Presence or absence, a length, or the like of the extended portion 24 can be appropriately selected and changed according to a configuration of the grasping portion 2 and other factors such as a size of grasping forceps (treatment tool) G.

A communication hole 24*a* communicating with the second through hole 12 formed in the cap 1 is formed in the extended portion 24, and through which the open-close operation wire 5 and the ejection operation wire 6 are inserted.

Further, in the present embodiment, the extended portion 24 is provided in the grasping portion 2, but the extended portion 24 May be configured to be provided in the cap 1.

The first main body portion 21*b* includes a contact pin 21*c* (FIG. 8). The contact pin 21*c* is provided at the proximal end of the first main body portion 21*b* and comes into contact with the anvil 22 in a closed state to restrict a movable range of the anvil 22.

As shown in FIG. 8, a first engagement groove 21*d* is a groove penetrating in the axial direction C of the open-close rotation shaft 23 in the first main body portion 21*b*. The first engagement groove 21*d* extends in the axial direction A.

The anvil 22 is attached to the stapling head 21 to be rotatable by the open-close rotation shaft 23. As shown in FIGS. 6 and 7, the anvil 22 includes a U-shaped member 22*a* formed in a substantially U shape, and a second main body portion 22*b* supporting the U-shaped member 22*a* to be rotatable.

The U-shaped member 22*a* is formed in a substantially U-shape, and both end parts thereof are coupled to the second main body portion 22*b*. In a closed state, a central portion of the U-shaped member 22*a* is disposed on a distal-end side of the stapling head 21. The central portion includes a second distal-end portion 22*c*. The second distal-end portion 22*c* is formed in a substantially rectangular parallelepiped shape. The second distal-end portion 22*c* extends in the axial direction C of the open-close rotation shaft 23. The staple receiving portion 4 is provided at the second distal-end portion 22*c*.

The second main body portion 22*b* is attached to the first main body portion 21*b* of the stapling head 21 to be rotatable by the open-close rotation shaft 23. A guide groove 22*d* into which the first main body portion 21*b* is inserted is formed in the second main body portion 22*b*. A second engagement groove 22*e* is formed in each of a pair of side plate portions 22*g* facing each other in the axial direction C with the guide groove 22*d* of the second main body portion 22*b* interposed therebetween.

The second engagement grooves 22*e* are grooves each penetrating in the axial direction C. As shown in FIG. 7, the second engagement grooves 22*e* are symmetrical with respect to the central axis O3 of the anvil 22. As shown in FIG. 8, the second engagement grooves 22*e* are each inclined toward the downward side B2 from the distal-end side to the proximal-end side in the axial direction A in a side view in a closed state.

As shown in FIGS. 2 and 4, the anvil 22 includes a pair of first guide portions 22*h* having a cubic shape. The pair of first guide portions 22*h* are displaced around an axis of the open-close rotation shaft 23 into a protruding orientation (FIG. 8) or a retracted orientation (FIG. 9) in accordance with opening and closing of the anvil 22.

As shown in FIG. 7, the pair of first guide portions 22*h* are positioned inside the pair of second main body portions 22*b* to which both end parts of the U-shaped member 22*a* are connected. As shown in FIG. 8, a part of the first guide portion 22*h* on the proximal-end side is coupled to the side plate portion 22*g* in which the second engagement groove 22*e* is formed. In a side view shown in FIG. 8, a first end surface 22*h*1 of the first guide portion 22*h* is coplanar with a first end surface 22*g*1 of the side plate portion 22*g*.

A width W1 of the first guide portion 22*h* in the axial direction C is smaller than the width W2 of the side plate portion 22*g* in the axial direction C (W1<W2). A second end surface 22*h*3 of the first guide portion 22*h* is coupled to a second end surface 22*g*2 of the side plate portion 22*g* via a third end surface 22*h*4 orthogonal to the second end surface 22*h*3. A notch portion 22*k* that enables the first guide portion 22*h* to avoid coming into contact with the contact pin 21*c* when the anvil 22 is opened or closed is formed between the first guide portion 22*h* and the side plate portion 22*g*.

Further, a shape of the first guide portion 22*h* is not limited to a cubic shape and can be changed as appropriate. Also, a protrusion height H and the width W1 of the first guide portion 22*h* are not limited to the height dimension shown in FIG. 8, and can be changed as appropriate.

As shown in FIG. 8, when the anvil 22 is in a closed state, the upper surface 22*h*2 of the first guide portion 22*h* protrudes in a direction in which the anvil 22 opens (to the upward side B1) with respect to an upper surface 22*f* of the stapling head 21 (protruding orientation). Also, when the first guide portion 22*h* is in the protruding orientation, the upper surface 22*h*2 thereof is positioned on the downward side B2 with respect to an upper surface 22*j* of the anvil 22.

Although it has been described that, when the first guide portion 22*h* is in the protruding orientation, the upper surface 22*h*2 thereof is positioned on the downward side B2 with respect to the upper surface 22*j* of the anvil 22, the upper surface 22*h*2 may be on the upward side B1 with respect to the upper surface 22*j* of the anvil 22. However, the upper surface 22*h*2 needs to be on the downward side B2 with respect to an optical axis A1 not to hinder a visual field of the endoscope 200.

As shown in FIG. 9, when the anvil 22 is in an open state, the first guide portion 22*h* does not protrude in the direction in which the anvil 22 opens (to the upward side B1) with respect to the stapling head 21 (retracted orientation). When the first guide portion 22*h* is in the retracted orientation, it is positioned at the same height as the upper surface 21*f* of the first main body portion 21*b* of the stapling head 21. Here, when the first guide portion 22*h* is in the retracted orientation, the first end surface 22*h*1 is coplanar with the upper surface 21*f* of the first main body portion 21*b* of the stapling head 21.

The pair of guide portions 22*h* are provided in the anvil 22, and one of the first guide portions 22*h* is present on a movement path of grasping forceps G.

When the first guide portion 22*h* is in the retracted orientation, the first end surface 22*h*1 may be on the downward side B2 with respect to the upper surface 21*f* of the first main body portion 21*b* of the stapling head 21.

As shown in FIG. 6, the anvil 22 has a visual space (pass-through space) 25 that passes through in an open-close direction R between the staple receiving portion 4 on the distal-end side and the open-close rotation shaft 23 on the proximal-end side. In the present embodiment, the visual space 25 is a space surrounded by sides of the U-shaped member 22*a* formed in a substantially U shape.

As shown in FIG. 8, the movable pin 27 is engaged with the first engagement groove 21*d* and the second engagement groove 22*e*, and advances and retracts in the axial direction A along the first engagement groove 21*d*. A distal end of the open-close operation wire 5 is attached to the movable pin 27. The movable pin 27 advances and retracts in the axial direction A due to an operation of the open-close operation wire 5, and in conjunction with this, the anvil 22 opens and closes as shown in FIGS. 8 and 9.

When the open-close operation wire 5 advances toward the distal-end side, as shown in FIG. 9, the movable pin 27 rotates the anvil 22 in an opening direction (R1) with the open-close rotation shaft 23 as a center to bring the grasping portion 2 into an open state. When the open-close operation wire 5 retracts toward the proximal-end side, as shown in FIG. 8, the movable pin 27 rotates the anvil 22 in a closing direction (R2) with the open-close rotation shaft 23 as a center to bring the grasping portion 2 into a closed state.

When the grasping portion 2 is in a closed state, the staple ejection portion 3 and the staple receiving portion 4 face each other in the vertical direction B as shown in FIG. 8. When the grasping portion 2 is in the closed state, a slight gap P is formed between the staple ejection portion 3 and the staple receiving portion 4. When the grasping portion 2 is in the closed state, an optical axis A1 of the objective lens 215 passes outside (the upward side B1 of) the stapling head 21 and the anvil 22. Also, when the grasping portion 2 is in the closed state, a central axis A2 of the forceps port 214 is at a position not overlapping the stapling head 21 but overlapping the anvil 22 in a front view.

As shown in FIG. 9, when the grasping portion 2 is in an open state, the staple receiving portion 4 is disposed on the proximal-end side with respect to the open-close rotation shaft 23. When the grasping portion 2 is in the open state, the staple receiving portion 4 is disposed on the proximal-end side with respect to the staple ejection portion 3. When the grasping portion 2 is in the open state, the optical axis A1 of the objective lens 215 passes through the visual space 25. Also, when the grasping portion 2 is in the open state, the central axis A2 of the forceps port 214 passes through the visual space 25.

Figure 10:
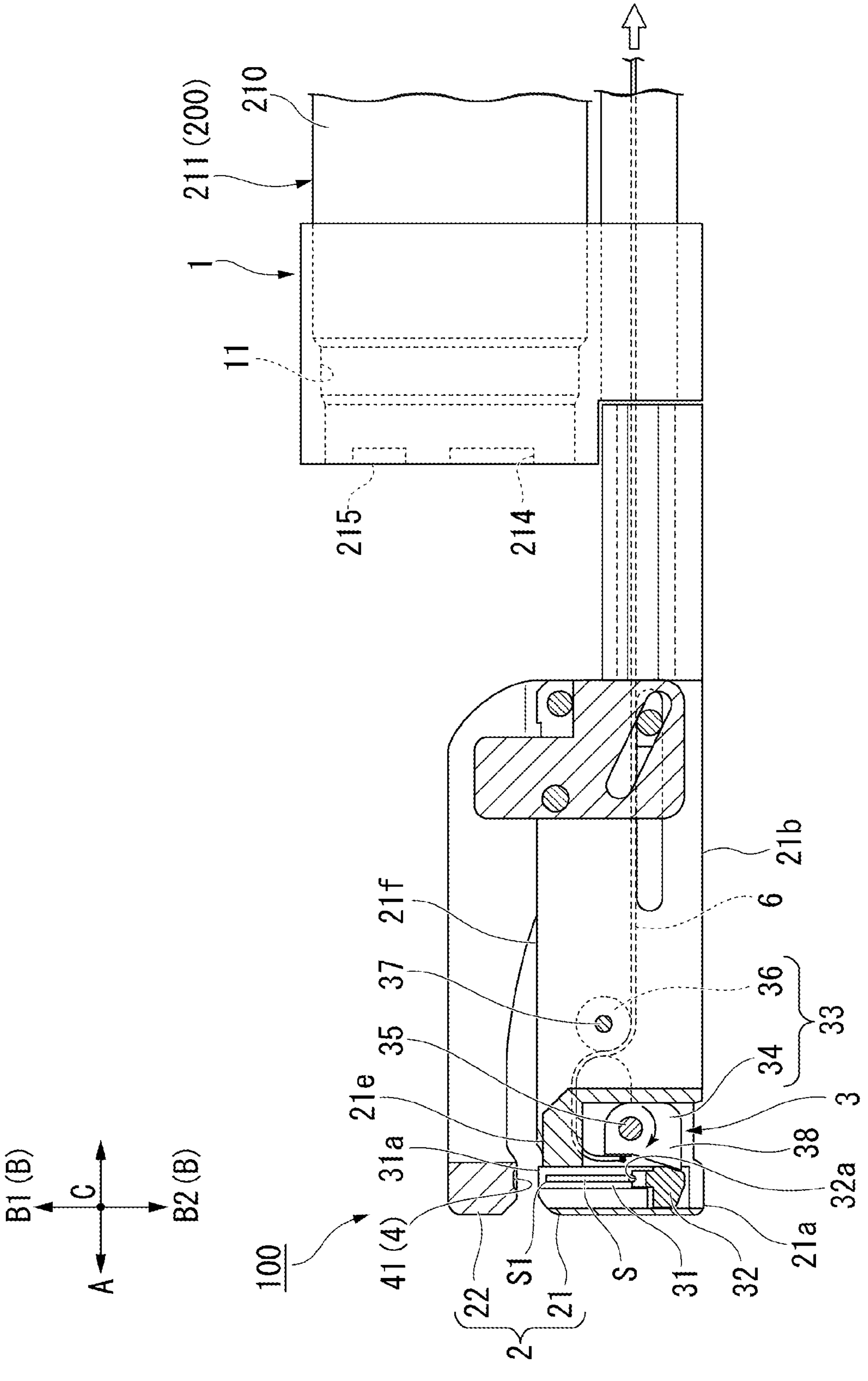
FIG. 10 is a cross-sectional view showing the grasping portion including a staple ejection portion.

FIG. 10 is a cross-sectional view showing the grasping portion 2 including the staple ejection portion 3. FIG. 10 shows a state before the ejection operation wire 6 is pulled.

The staple ejection portion 3 is provided at the first distal-end portion 21*a* of the stapling head 21, and can store and eject the staple S. The staple ejection portion 3 includes a staple storage portion 31, a linear movement member 32, and a rotation member 33.

The staple storage portion 31 is a space that stores the staple S provided at the first distal-end portion 21*a* of the stapling head 21. As shown in FIGS. 6 and 7, the stapling head 21 includes two staple storage portions 31 formed to be aligned in the axial direction C and capable of storing two U-shaped staples S.

The staple storage portion 31 opens in the vertical direction B at the opening 31*a* provided on the upper surface 21*e* of the first distal-end portion 21*a*. The staple S is stored in the staple storage portion 31 through the opening 31*a*. The staple S is stored in the staple storage portion 31 with needle tips S1 of the staple S facing the upward side B1.

The staple storage portion 31 is formed in a rectangular shape with short sides extending in the axial direction A and long sides extending in the axial direction C in a plan view. In the staple S stored in the staple storage portion 31, the needle tips S1 at both ends are disposed in the axial direction C.

The linear movement member 32 is a member accommodated in a bottom part of the staple storage portion 31 and is movable in the vertical direction B in an internal space of the staple storage portion 31. The linear movement member 32 includes a recessed portion 32*a* that supports the staple S to the upward side B1. The staple S stored in the staple storage portion 31 is fitted into the recessed portion 32*a*.

A first pulley 34 and a second pulley 36 as the rotation member 33 are rotatably attached inside the stapling head 21. The first pulley 34 and the second pulley 36 rotate to move the linear movement member 32 in the vertical direction B. A distal end of the ejection operation wire 6 is coupled to the first pulley 34. When the ejection operation wire 6 is pulled in an arrow direction in FIG. 10, the first pulley 34 can be made to rotate.

The second pulley 36 is rotatably attached inside the stapling head 21, and the first pulley 34 is disposed on a distal-end side with respect to the second pulley 36. A rotation shaft 35 of the first pulley 34 and a rotation shaft 37 of the second pulley 36 extend in the axial direction C and are substantially parallel to the open-close rotation shaft 23 of the grasping portion 2. The first pulley 34 has a protruding portion 38, which supports the linear movement member 32 from the downward side B2, on the distal-end side.

The distal end of the ejection operation wire 6 is coupled to the upward side B1 above the rotation shaft 35 at the first pulley 34. The ejection operation wire 6 extends from the first pulley 34 to the ejection operation unit 270 shown in FIG. 1 via the second pulley 36 and passing through the second through hole 12. The reason for providing the second pulley 36 is to adjust a position of the ejection operation wire 6 for smoothly guiding it into the second through hole 12, and to reduce frictional resistance when the ejection operation wire 6 is guided into the second through hole 12. Therefore, the same effect can be obtained even when only the first pulley 34 is used as the rotation member 33 and a member having an R shape with a high degree of slidability and having reduced friction is provided in place of the second pulley 36.

Figure 11:
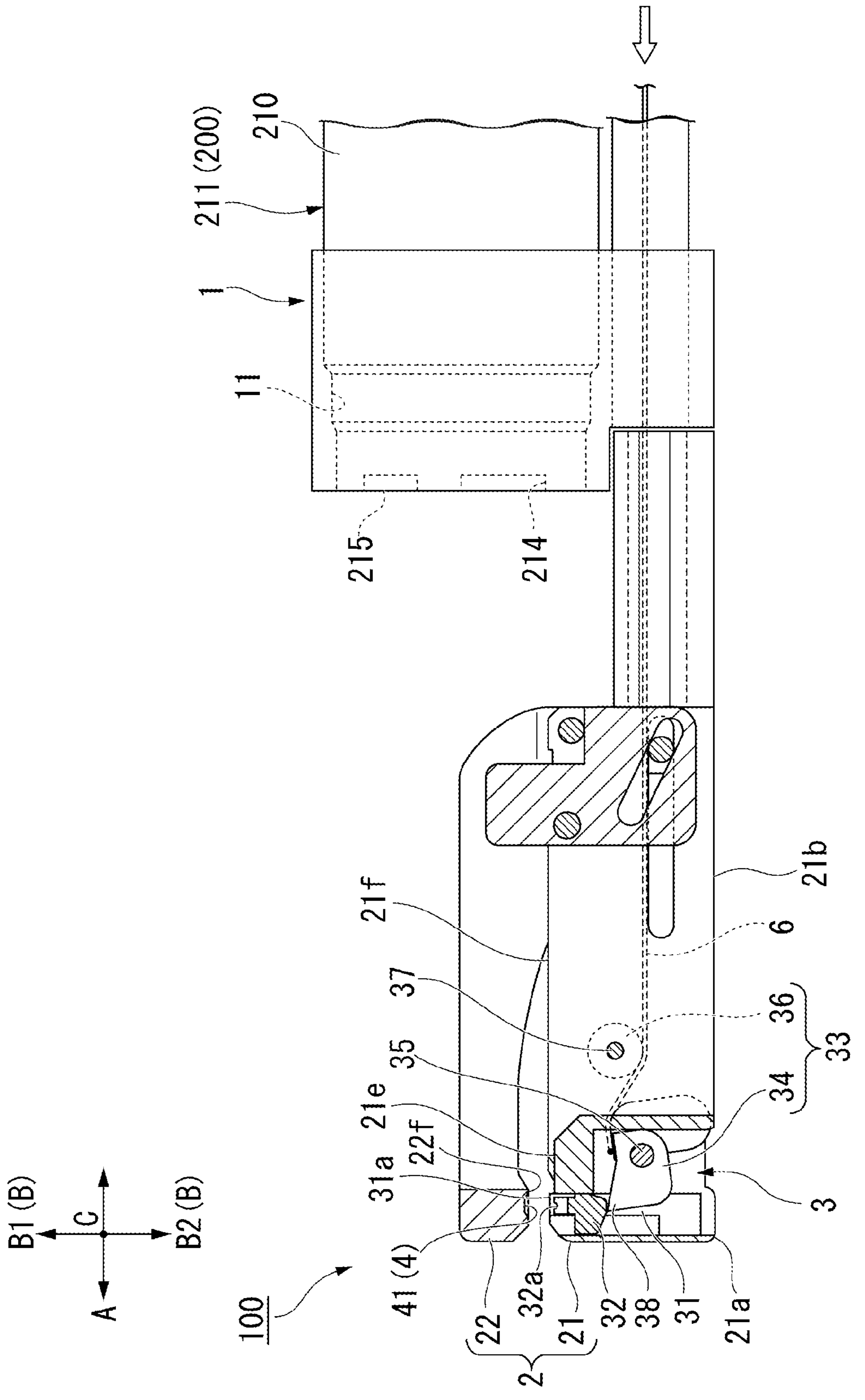
FIG. 11 is a cross-sectional view showing the grasping portion in which an ejection operation wire is pulled.

FIG. 11 is a cross-sectional view showing the grasping portion 2 in which the ejection operation wire 6 is pulled.

When the ejection operation wire 6 is pulled, a part of the first pulley 34 on the upward side B1 rotates to the proximal-end side, and a part of the first pulley 34 on the downward side B2 rotates to the distal-end side. As a result, the protruding portion 38 of the first pulley 34 pushes up the linear movement member 32 to the upward side B1, and the stored staple S is ejected from the opening 31*a* to the upward side B1.

The staple receiving portion 4 is provided on a lower surface of the second distal-end portion 22*c* of the anvil 22. A plurality of pockets 41 that can receive the staples S (FIG. 10) ejected from the staple ejection portion 3 are provided in the staple receiving portion 4. In the present embodiment, two U-shaped staples are ejected from the staple ejection portion 3. Therefore, four pockets 41 (FIG. 7) are provided in the staple receiving portion 4. When the grasping portion 2 is in the closed state, the opening 31*a* through which the staples S (FIG. 10) are ejected and the pockets 41 of the staple ejection portion 3 face each other in the vertical direction B.

Operation of Medical Stapler 100

Figure 12:
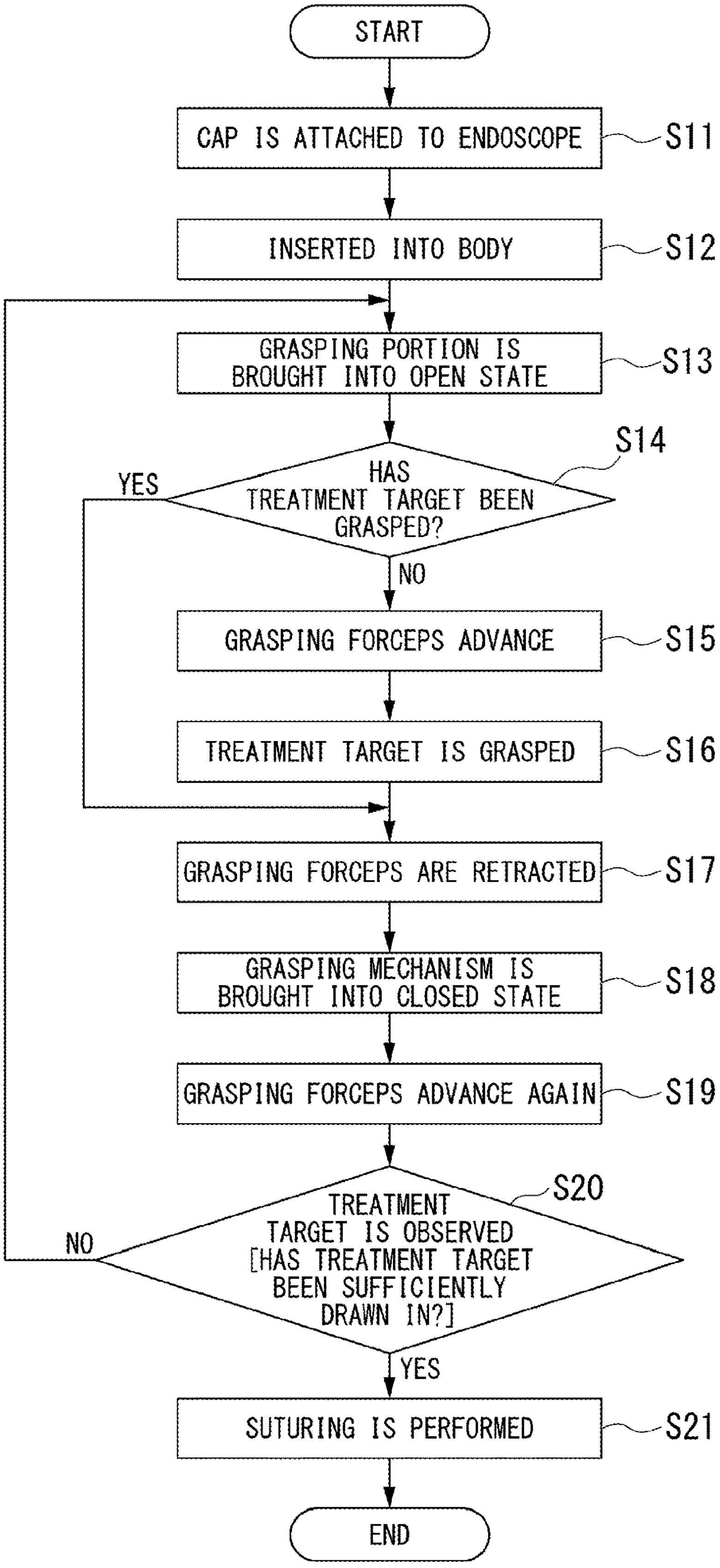
FIG. 12 is a flowchart showing a manipulation procedure performed by an operator using the medical stapler.

Next, an operation of the medical stapler 100 will be described. FIG. 12 is a flowchart showing a manipulation procedure performed by the operator using the medical stapler 100. FIGS. 13 to 18 are views showing an operation of the medical stapler 100.

Hereinafter, an operation of the medical stapler 100 will be described along the flowchart of FIG. 12 while referring to FIGS. 13 to 18.

First, the operator attaches the medical stapler 100 to the distal-end portion 211 of the endoscope 200 (attachment step S11). The operator inserts the endoscope 200 to which the medical stapler 100 is attached into the body (insertion step S12).

Figure 13:
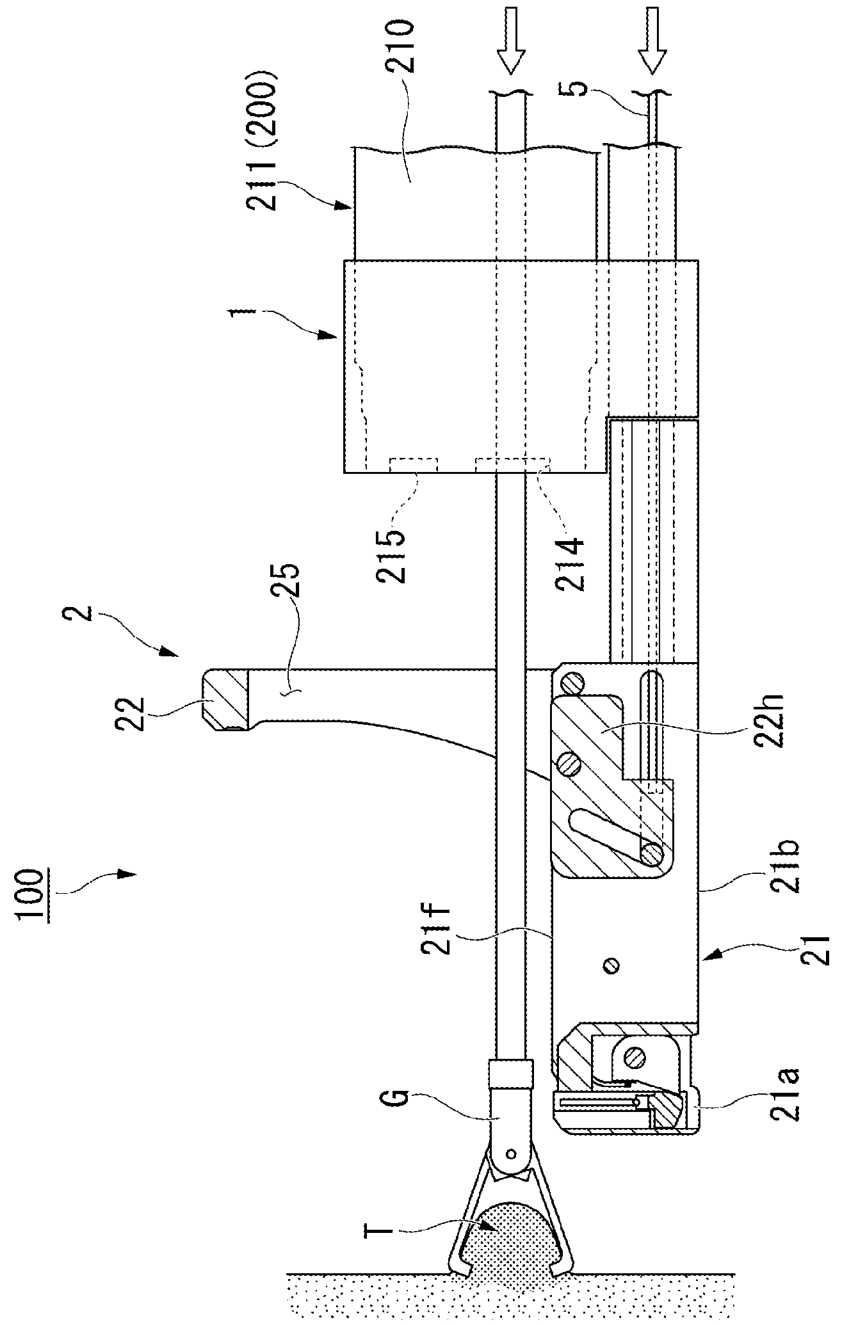
FIG. 13 is a view showing an operation of the medical stapler.

Next, as shown in FIG. 13, the operator brings the distal-end portion 211 of the endoscope 200 to which the medical stapler 100 is attached closer to a treatment target T. The treatment target T is, for example, a part of a tissue inside the body.

The operator operates the open-close operation unit 250 shown in FIG. 1 to advance the open-close operation wire 5, thereby opening the anvil 22 to bring the grasping portion 2 into an open state and placing the first guide portion 22*h* in the retracted orientation (first open-close step S13).

When the medical stapler 100 is inserted into the body for the first time, since the treatment target T is not grasped by the grasping forceps G (grasp ascertaining step S14: No), an advancing step S15 is subsequently performed.

After the grasping portion 2 is brought into the open state, the operator causes the grasping forceps G to protrude (advance) from the forceps port 214 and approach the treatment target T (first advancing step S15). The operator can advance the grasping forceps G while ascertaining a position of the treatment target T via the visual space 25 using the imaging unit of the endoscope 200. Since the first guide portion 22*h* is in the retracted orientation when the grasping portion 2 is in an open state, there is no protruding object on the stapling head 21 side and there is no obstacle to hinder observation. Therefore, the operator can satisfactorily observe the treatment target T via the visual space 25. The operator grasps the treatment target T with the grasping forceps G (grasping step S16).

Next, as shown in FIG. 13, the operator retracts the grasping forceps G with the treatment target T grasped by the grasping forceps G (retracting step S17). The operator retracts the grasping forceps G so that a distal end of the grasping forceps G is disposed on the proximal-end side with respect to the first guide portion 22*h*.

Figure 14:
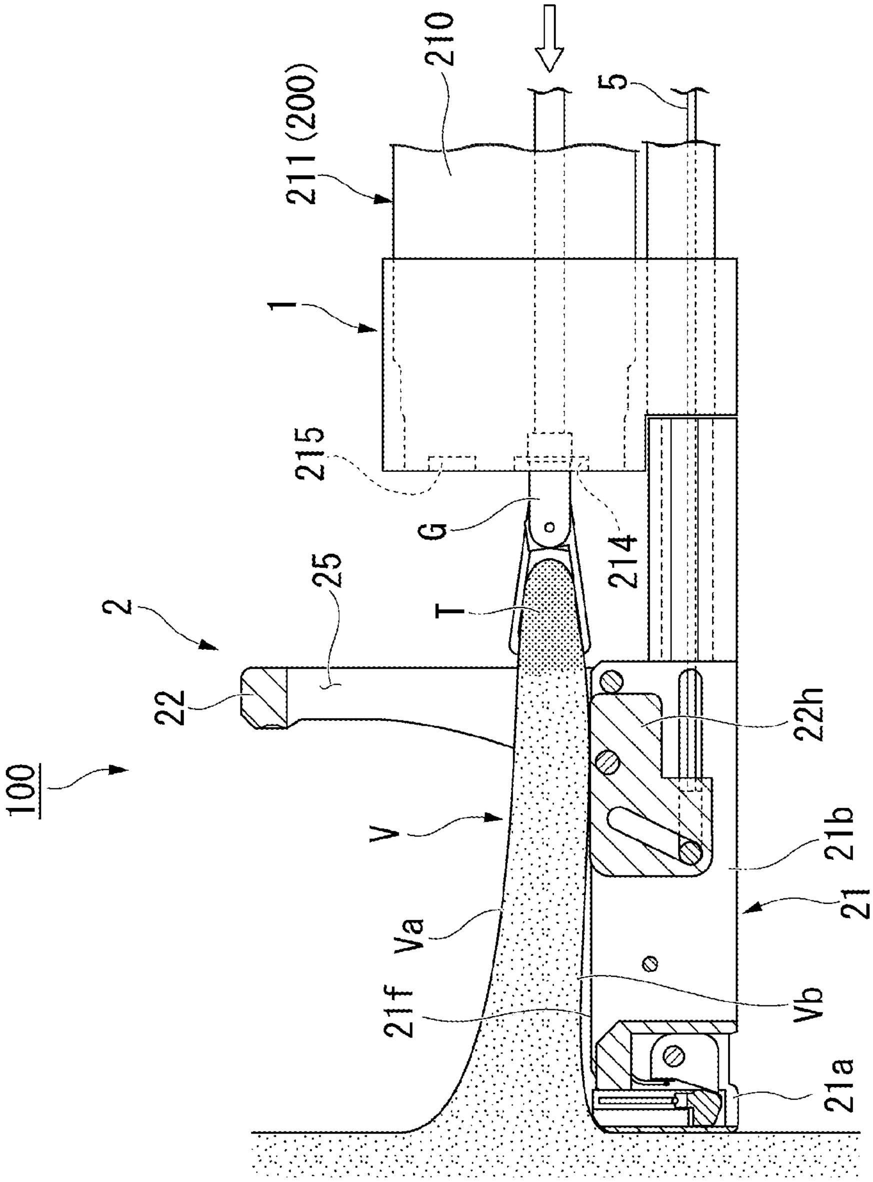
FIG. 14 is a view showing an operation of the medical stapler.

Next, as shown in FIG. 14, the operator brings the grasping portion 2 into a closed state by operating the open-close operation unit 250 shown in FIG. 1 to retract the open-close operation wire 5, thereby placing the first guide portion 22*h* in the protruding orientation (second open-close step S18). The first guide portion 22*h* assumes the protruding orientation at the same time as the grasping portion 2 is brought into a closed state, and protrudes to the upward side B1 with respect to the stapling head 21 within the visual space 25 of the anvil 22 in the closed state. A tissue V containing the treatment target T grasped by the grasping forceps G is sandwiched between the staple ejection portion 3 of the stapling head 21 and the staple receiving portion 4 of the anvil 22.

When the grasping portion 2 is in the closed state, since a part of the tissue V of the treatment target T grasped by the grasping forceps G can be accommodated in the visual space 25 formed inside the anvil 22, there is an effect that the treatment target T sandwiched between the staple ejection portion 3 and the staple receiving portion 4 is less likely to lose.

When the grasping portion 2 is in the closed state, the optical axis A1 of the objective lens 215 of the imaging unit passes outside (the upward side B1) of the stapling head 21 and the anvil 22. Therefore, even when the grasping portion 2 is in the closed state, the operator can observe the tissue V containing the treatment target T via the imaging unit of the endoscope 200. At this time, the operator can observe a surface Va (a surface on a side opposite to the stapling head 21) of the tissue V containing the treatment target T using the imaging unit.

Figure 15:
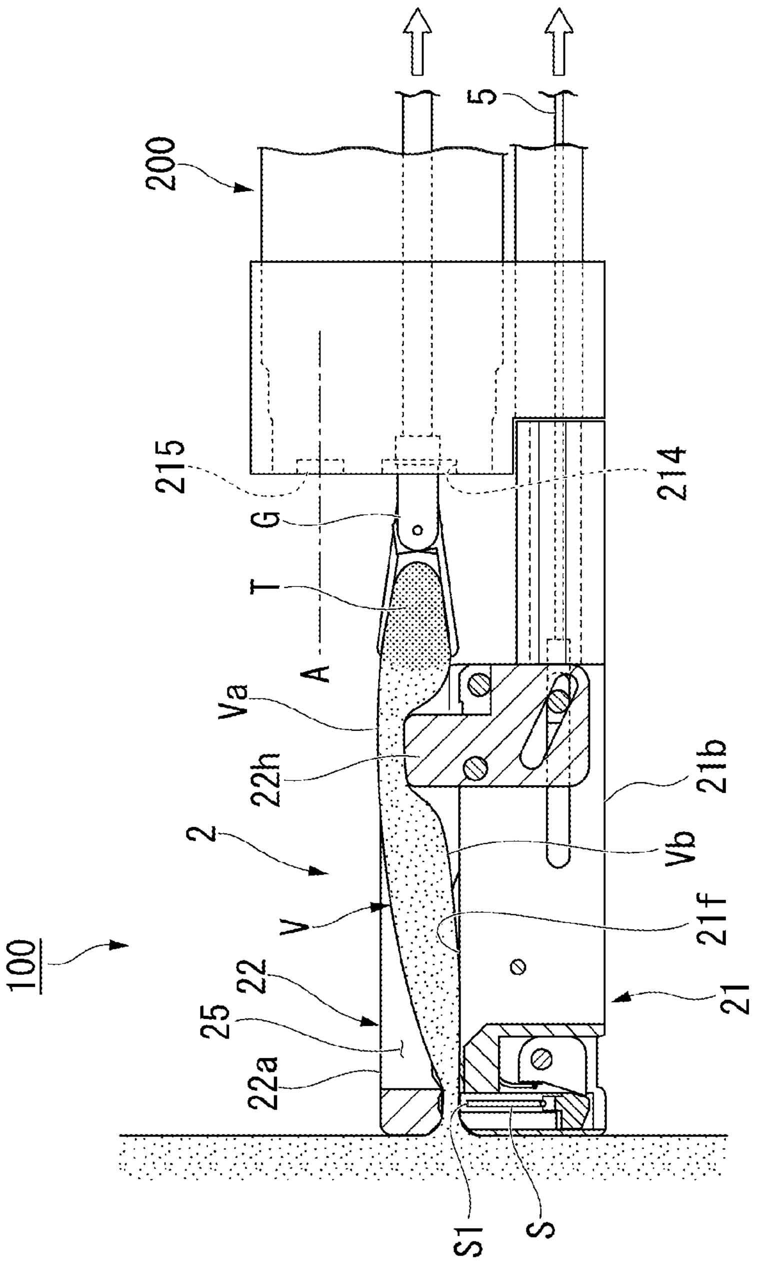
FIG. 15 is a view showing an operation of the medical stapler.
Figure 16:
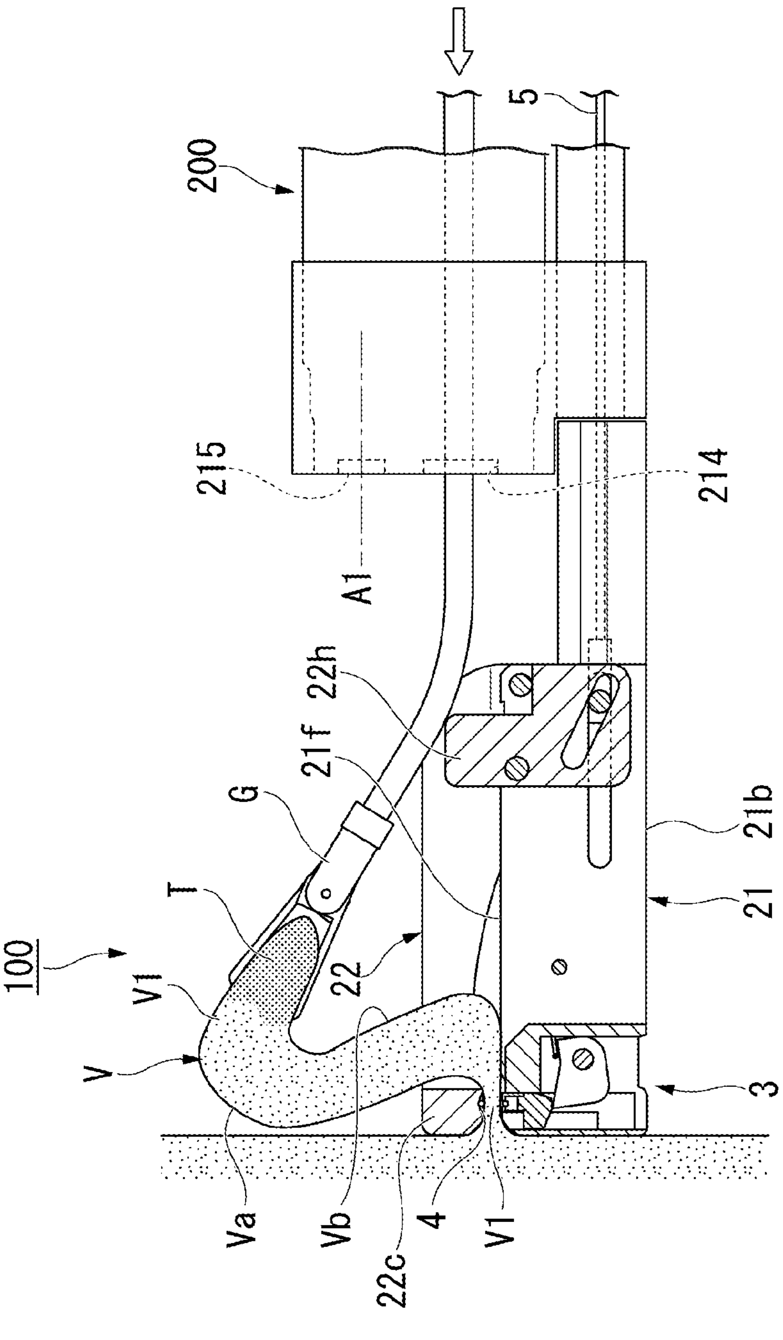
FIG. 16 is a view showing an operation of the medical stapler.

Next, as shown in FIG. 15, the operator advances the grasping forceps G again to move the grasping forceps G to the distal-end side with respect to the first guide portion 22*h* while keeping the grasping portion 2 in the closed state (second advancing step S19). At this time, when the grasping forceps G advance until the grasping forceps G ride on the first guide portion 22*h* in the protruding orientation, the distal-end side of the grasping forceps G is lifted to the upward side B1. As shown in FIG. 16, the grasping forceps G are lifted by the first guide portion 22*h* in the protruding orientation, which is present on an advance-retraction path. The grasping forceps G are lifted by one of the pair of first guide portions 22*h*. As shown in FIG. 15, when the grasping forceps G are lifted by the first guide portion 22*h*, the tissue V containing the treatment target T grasped by the grasping forceps G is lifted to the upward side B1 with respect to the anvil 22 in the closed state. At this time, it is preferable to lift the tissue V so that it is placed on the second distal-end portion 22*c* of the anvil 22. Therefore, the tissue V grasped by the grasping forceps G can be turned up.

A back surface Vb (surface facing the stapling head 21) side of the tissue V containing the treatment target T lifted by the grasping forceps G faces the objective lens 215 in a direction of the optical axis A1. The operator can observe the back surface Vb of the tissue V containing the treatment target T lifted by the grasping forceps G using the imaging unit of the endoscope 200 (observation step S20). The operator can ascertain whether or not the entire treatment target T has been drawn into the visual space 25 using the grasping forceps G. That is, it can be ascertained whether or not the treatment target T is present at a suture position at which the staple ejection portion 3 and the staple receiving portion 4 face each other. The operator performs the next suturing step S21 after ascertaining that the treatment target T is not contained in a portion sandwiched between the staple ejection portion 3 and the staple receiving portion 4.

In the observation step 20 described above, if it is ascertained that the treatment target T is insufficiently drawn in and the treatment target T is present at the suture position, the processing returns to the first open-close step S13 to bring the grasping portion 2 into an open state. The operator determines in grasp ascertaining step S14 to proceed to retracting step S17 due to the state in which the treatment target T is grasped by the grasping forceps G (grasp ascertaining step S14: Yes), and further retracts the grasping forceps G (retracting step S17) while grasping the treatment target T to further draw the tissue V containing the treatment target T into the grasping portion 2. Thereafter, the grasping portion 2 is brought into a closed state (second open-close step S18), the treatment target T is lifted by advancing the grasping forceps G until the grasping forceps G ride on the first guide portion 22*h* that has protruded (second advancing step S19), and the back surface side of the treatment target T is observed again (observation step S20). The operator performs steps S13 to S20 until it is ascertained that the treatment target T is not contained in the portion sandwiched between the staple ejection portion 3 and the staple receiving portion 4. At this time, steps S15 and S16 are skipped.

Next, in a state in which a tissue V1 around the treatment target T at a portion that does not contain the treatment target T among the tissue V pulled by the grasping forceps G is sandwiched between the staple ejection portion 3 and the staple receiving portion 4, the operator operates the ejection operation unit 270 to pull the ejection operation wire 6, and thereby, the staple S stored in the staple ejection portion 3 is ejected toward the staple receiving portion 4. At this time, the staple S may be ejected from the stapling head 21 a plurality of times. The needle tips S1 of the staple S penetrate the tissue V1 around the treatment target T and are bent by coming into contact with the pockets 41 of the staple receiving portion 4. As a result, the tissue V containing the treatment target T is sutured. Therefore, the entire treatment target T is sutured (suturing step S21).

Figure 17:
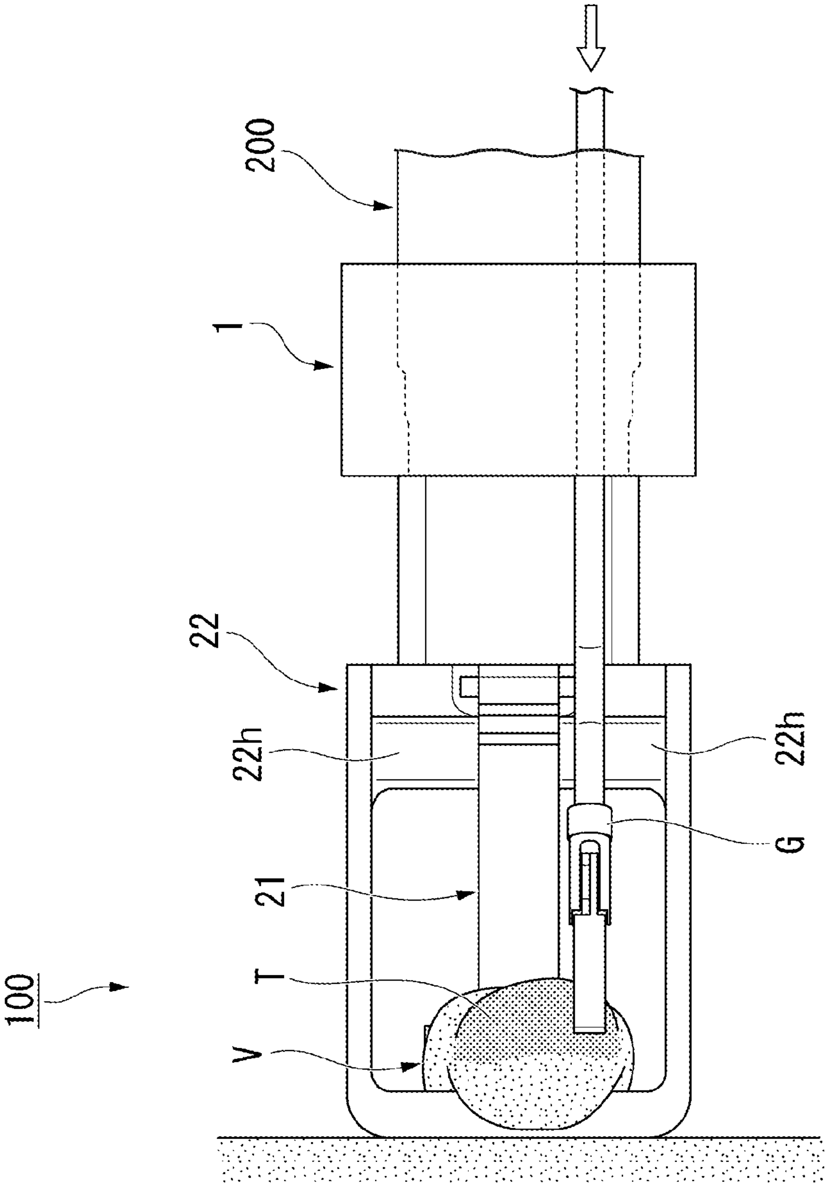
FIG. 17 is a view showing an operation of the medical stapler.
Figure 18:
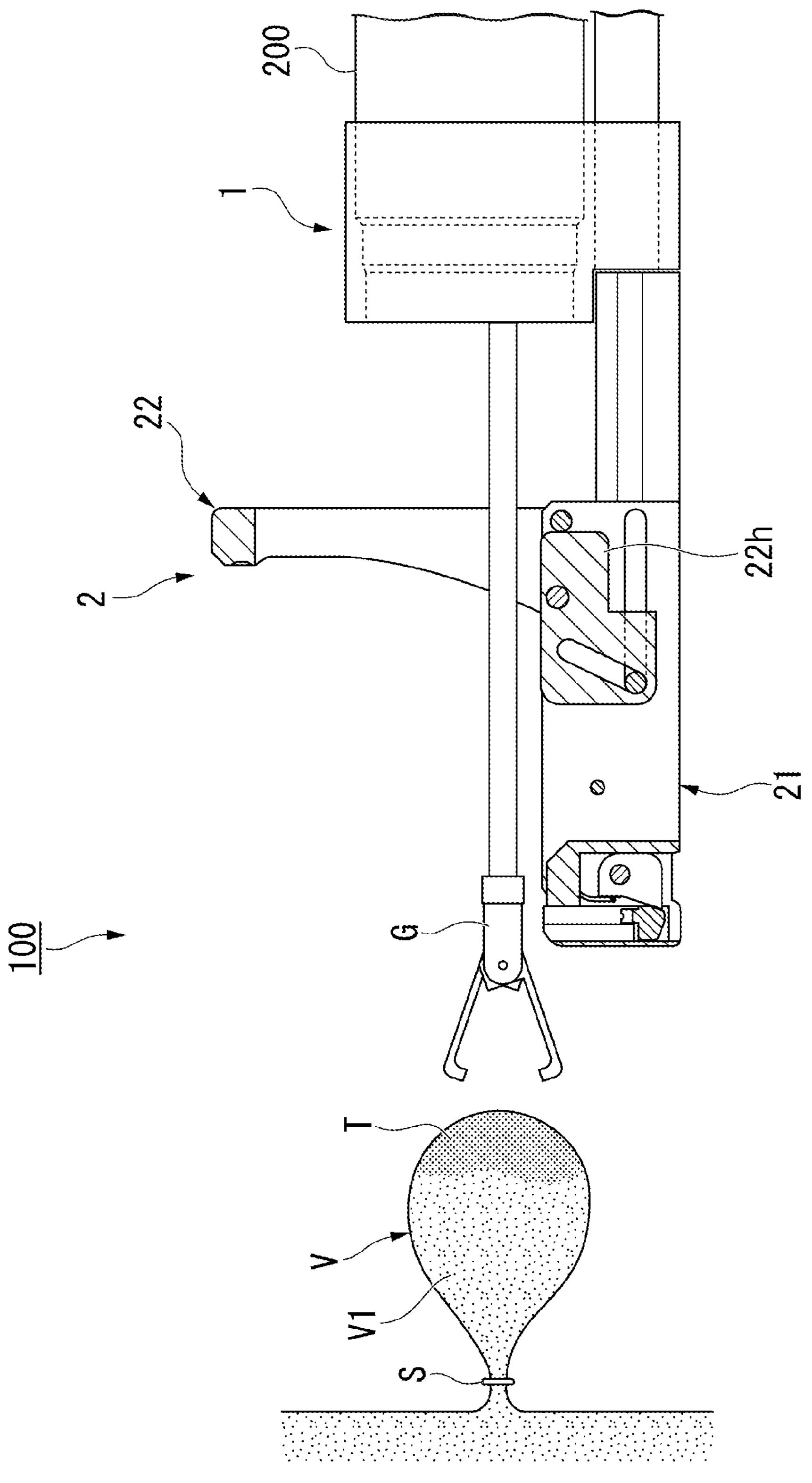
FIG. 18 is a view showing an operation of the medical stapler.

Next, as shown in FIG. 17, the operator operates the open-close operation unit 250 shown in FIG. 1 to bring the grasping portion 2 into an open state again. The operator opens the grasping forceps G to release the grasp on the treatment target T, thereby completing the suturing treatment. Thereafter, the operator removes the medical stapler 100 and endoscope 200 from the inside of the body.

According to the medical stapler 100 of the present embodiment, when the treatment target T grasped by the grasping forceps G is lifted to the upward side B1 by the first guide portion 22*h*, a state of the back surface (surface facing the stapling head 21) of the treatment target T can be visually observed using the imaging unit. Therefore, the treatment target T can be sufficiently drawn into the grasping portion 2 by the grasping forceps G while ascertaining the suture position. That is, the operator can perform suturing on the tissue V1 around the treatment target T in a state of containing the entire treatment target T. Therefore, the treatment target T can be completely excised, and a treatment effect can be improved.

Also, according to the medical stapler 100 of the present embodiment, since the first guide portion 22*h* is provided in the anvil 22, and the anvil 22 with the first guide portion 22*h* of the present embodiment can be employed in an existing structure, the costs can be suppressed to be low.

According to the medical stapler 100 of the present embodiment, since an insertion diameter of the medical stapler 100 with the grasping portion 2 in a closed state is substantially the same as that of the distal-end portion 211 of the endoscope 200, it can be easily inserted into the body such as the digestive tract. Also, even if the grasping portion 2 of the medical stapler 100 is in an open state, the operator can observe the treatment target T via the imaging unit of the endoscope 200 and can treat the treatment target T by causing the grasping forceps G to protrude from the forceps port 214.

While the first embodiment of the present disclosure has been described in detail as above with reference to the drawings, the specific configurations are not limited to the embodiment and may include design changes or the like within a range not departing from the gist of the present invention. Also, the components shown in the embodiment and modified examples described above can be configured by appropriately combining them.

For example, a shape of the grasping portion 2 is not limited to the aspect of the first embodiment. Hereinafter, modified examples of the grasping portion 2 will be described. Further, in the following description, components that are common to those already described will be denoted by the same reference signs and duplicate description will be omitted.

Modified Example 1

For example, in the embodiment described above, the pair of first guide portions 22*h* have been formed in a cubic shape, but a shape of the first guide portions 22*h* is not limited thereto.

Figure 19A:
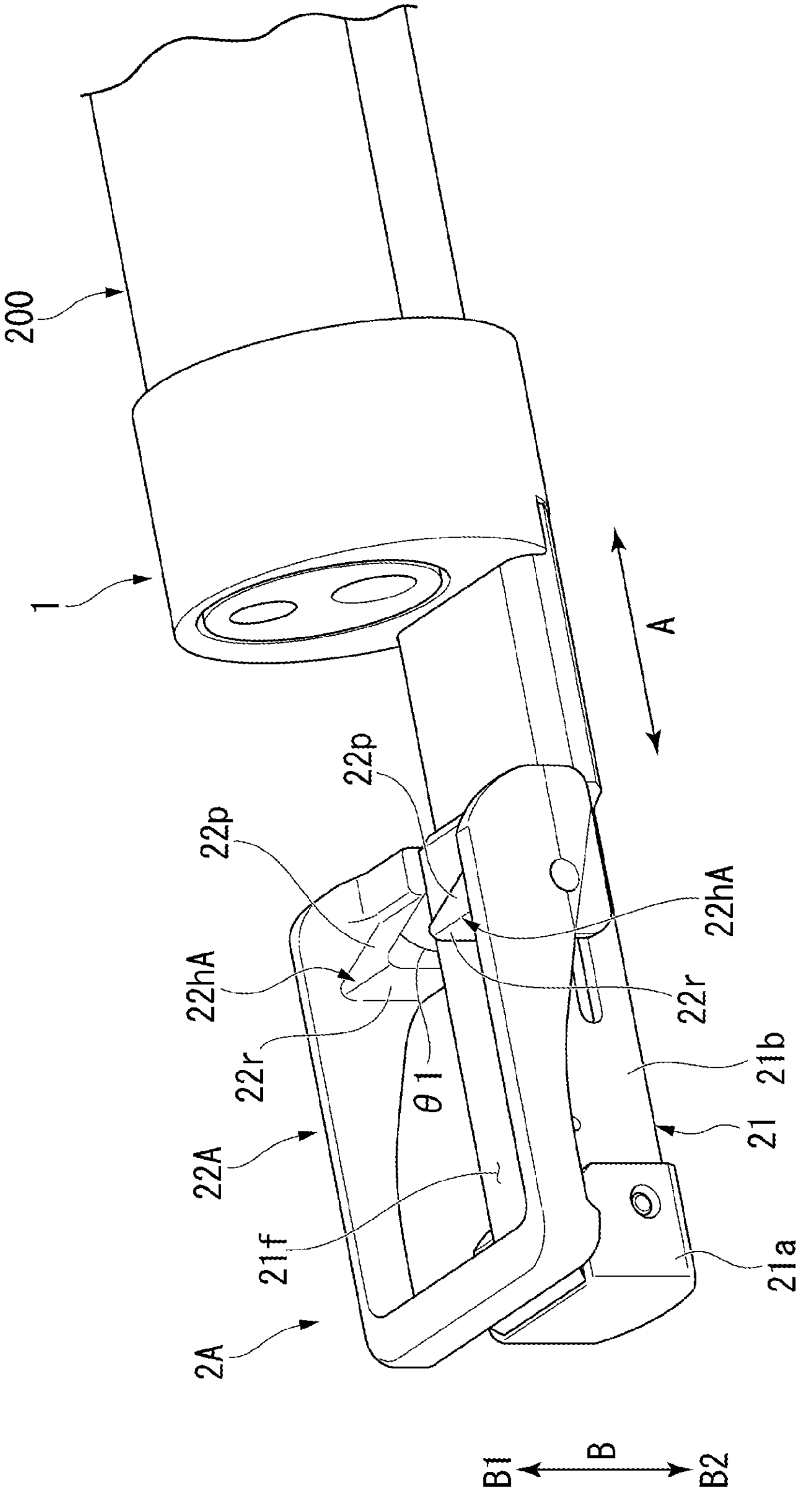
FIG. 19A is a perspective view showing a grasping portion in modified example 1.
Figure 19B:
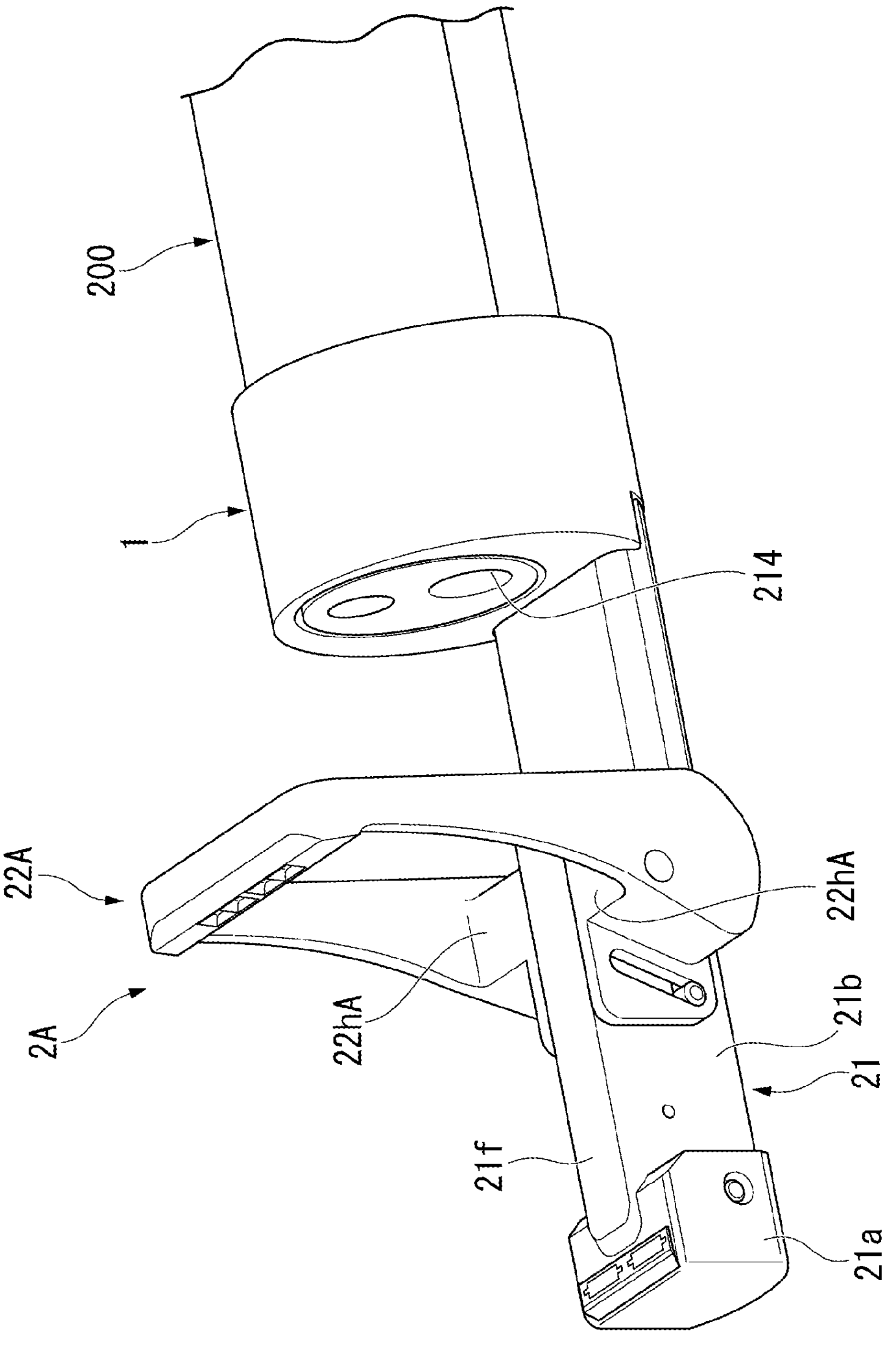
FIG. 19B is a perspective view showing the grasping portion in modified example 1.

FIGS. 19A and 19B are perspective views showing a grasping portion 2A in modified example 1.

Modified example 1 of the first embodiment will be described with reference to FIGS. 19A and 19B.

As shown in FIGS. 19A and 19B, an anvil 22A of the grasping portion 2A includes a first guide portion 22*h*A having a triangular shape in a side view. As shown in FIG. 19A, the first guide portion 22*h*A includes a side surface 22*r* orthogonal to a length direction (axial direction A) of the anvil 22A and extending to the upward side B1, and a first inclined surface 22*p* inclined in a direction away from the side surface 22*r* from a distal end to a proximal-end side of the side surface 22*r*.

As shown in FIG. 19A, an inclination angle θ1 of the first inclined surface 22*p* with respect to a horizontal direction is appropriately set according to types of treatment tool or the like.

As shown in FIG. 19A, when the grasping portion 2A is in a closed state, the pair of first guide portions 22*h*A protrude to the upward side B1 with respect to the stapling head 21 and are in a protruding orientation. The first inclined surface 22*p* in each of the first guide portions 22*h*A faces the distal-end portion 211 of the endoscope 200.

As shown in FIG. 19B, when the grasping portion 2A is in an open state, the pair of first guide portions 22*h*A are both in a retracted orientation. The pair of first guide portions 22*h*A are displaced in conjunction with rotation of the anvil 22A in a closing direction, and when the grasping portion 2A is in an open state, a portion thereof protruding to the upward side B1 from the stapling head 21 disappears completely, and the pair of first guide portions 22*h*A are placed in a retracted orientation completely hidden by the stapling head 21.

In modified example 1, it is the same as the first embodiment in that the pair of first guide portions 22*h*A protrude to the upward side B1 with respect to the stapling head 21 when the grasping portion 2A is in a closed state. The first inclined surfaces 22*p* of the pair of first guide portions 22*h*A in the protruding orientation coincide with each other in the axial direction A. Each of the first inclined surfaces 22*p* is inclined to the upward side B1 with distance away from the endoscope 200. Therefore, the grasping forceps G (FIG. 16) that have advanced from the forceps port 214 are lifted to the upward side B1 along the first inclined surface 22*p* of either one of the first guide portions 22*h*A.

According to the configuration of modified example 1, since the grasping forceps G are smoothly lifted to the upward side B1 by the first inclined surface 22*p* of the first guide portion 22*h*A, the operation by the operator is facilitated.

Modified Example 2

For example, in the first embodiment, the pair of first guide portions 22*h* are provided only on the anvil 22 side, but they may be provided on other components. A grasping portion 2B according to modified example 2 has a different shape of the stapling head compared to the grasping portion 2A according to modified example 1.

Figure 20A:
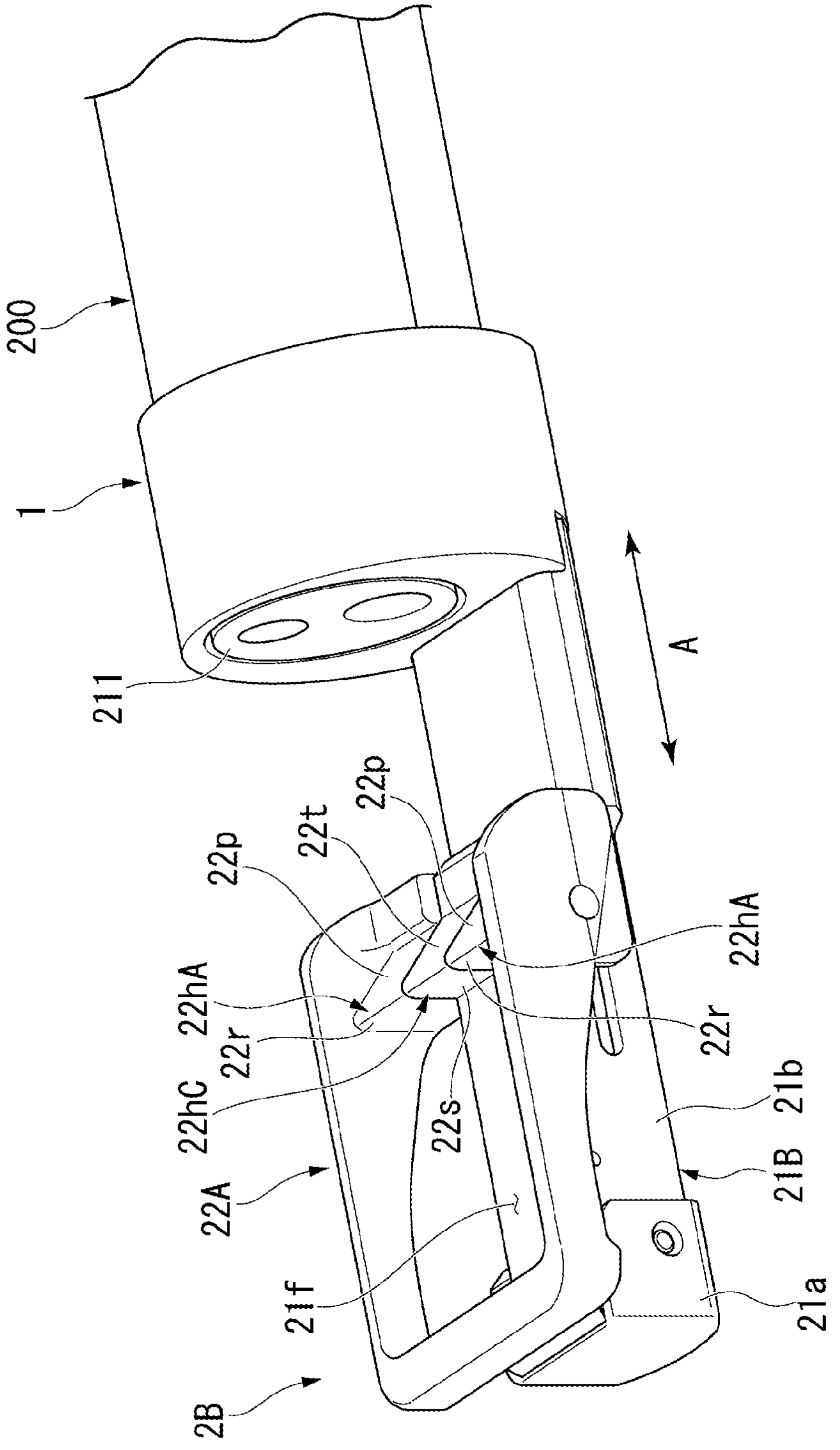
FIG. 20A is a perspective view showing a grasping portion in modified example 2.
Figure 20B:
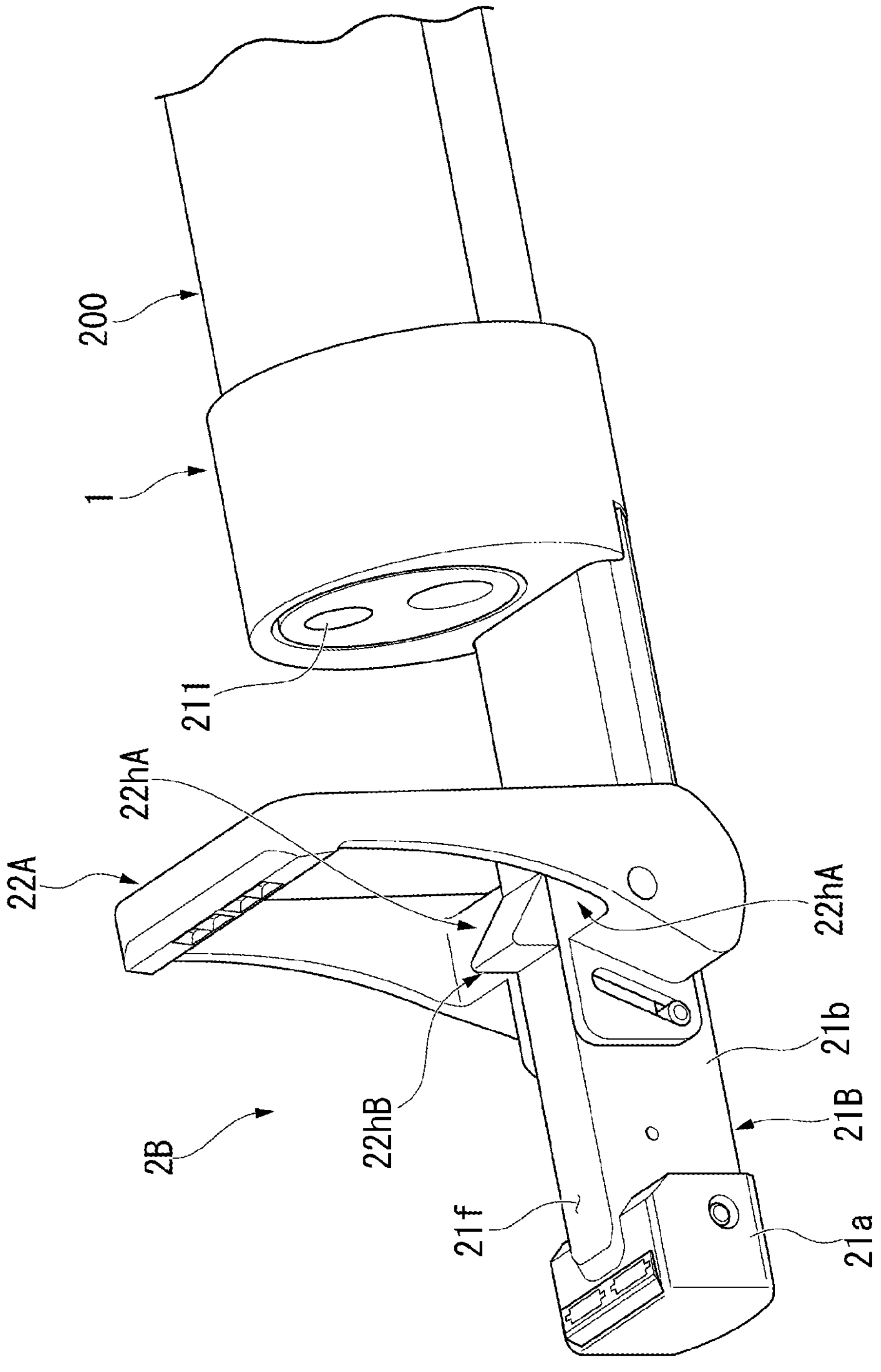
FIG. 20B is a perspective view showing the grasping portion in modified example 2.

FIGS. 20A and 20B are perspective views showing the grasping portion 2B of modified example 2.

Hereinafter, modified example 2 will be described with reference to FIGS. 20A and 20B.

As shown in FIGS. 20A and 20B, the stapling head 21B of the grasping portion 2B has one second guide portion 22*h*B on the proximal-end side. The second guide portion 22*h*B on the stapling head 21 side has a triangular shape in a side view similarly to the pair of first guide portions 22*h*A provided on the anvil 22A, and is formed to protrude from the upper surface 21*f* of the first main body portion 21*b*.

The second guide portion 22*h*B includes a side surface 22*s* orthogonal to a length direction (axial direction A) of the stapling head 21 and extending to the upward side B1, and a second inclined surface 22*t* that is inclined toward the downward side B2 from an upper end of the side surface 22*s* as it goes to a proximal-end side of the stapling head 21C. A position of the second inclined surface 22*t* of the second guide portion 22*h*B in the axial direction A substantially coincides with that of the first inclined surface 22*p* of each of the pair of first guide portions 22*h*A on the anvil 22A side.

As shown in FIG. 20A, when the grasping portion 2B is in a closed state, the pair of first guide portions 22*h*A of the anvil 22A are disposed on both sides of the second guide portion 22*h*B of the stapling head 21.

As shown in FIG. 20B, when the grasping portion 2B is in an open state, only the pair of first guide portions 22*h*A on the anvil 22 side are in a retracted orientation while the second guide portion 22*h*B on the stapling head 21 side remains in a protruding orientation.

According to the configuration of modified example 2, when the grasping portion 2B is in a closed state, since the second guide portion 22*h*B on the stapling head 21 side is present between the pair of first guide portions 22*h*A on the anvil 22A side, when the above-described first advancing step S15 (FIG. 12) is performed with the grasping portion 2B in the closed state, it is possible to prevent the grasping forceps G from passing between the pair of first guide portions 22*h*A and advancing along the upper surface 21*f* of the first main body portion 21*b* of the stapling head 21.

Also, it is possible to prevent the grasping forceps G, which have once been lifted by one of the first guide portions 22*h*A, from falling between the pair of first guide portions 22*h*A. Due to these pair of first guide portions 22*h*A and second guide portion 22*h*B, it is possible to reliably lift the grasping forceps G that have grasped the treatment target T to the upward side B1 to ascertain the suture position.

Also, since the grasping forceps G are lifted by one of these three guide portions 22*h*A, 22*h*B, and 22*h*A, even an operator who is not accustomed to the operation can easily ascertain the suture position simply by advancing the grasping forceps G. Also, positioning when the cap 1 is attached to the distal-end portion 211 of the endoscope 200 is facilitated, and work efficiency is improved.

Modified Example 3

For example, in the first embodiment, the pair of first guide portions 22*h* are configured to be provided on the anvil 22 side, but the present disclosure is not limited to the configuration. A grasping portion 2C of modified example 3 differs from the first embodiment in that the pair of first guide portions 22*h* are integrated.

Figure 21A:
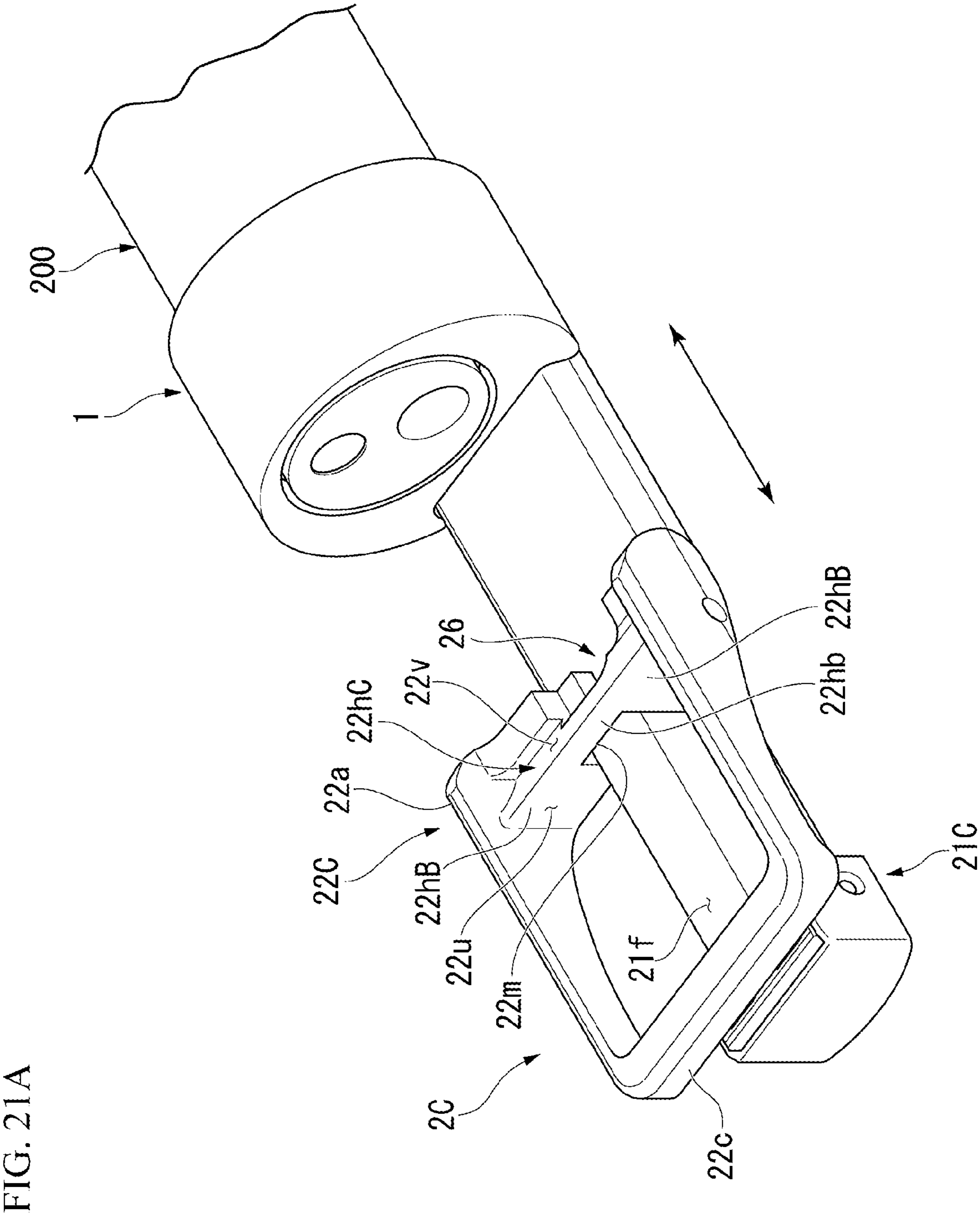
FIG. 21A is a perspective view showing a grasping portion in modified example 3.
Figure 21B:
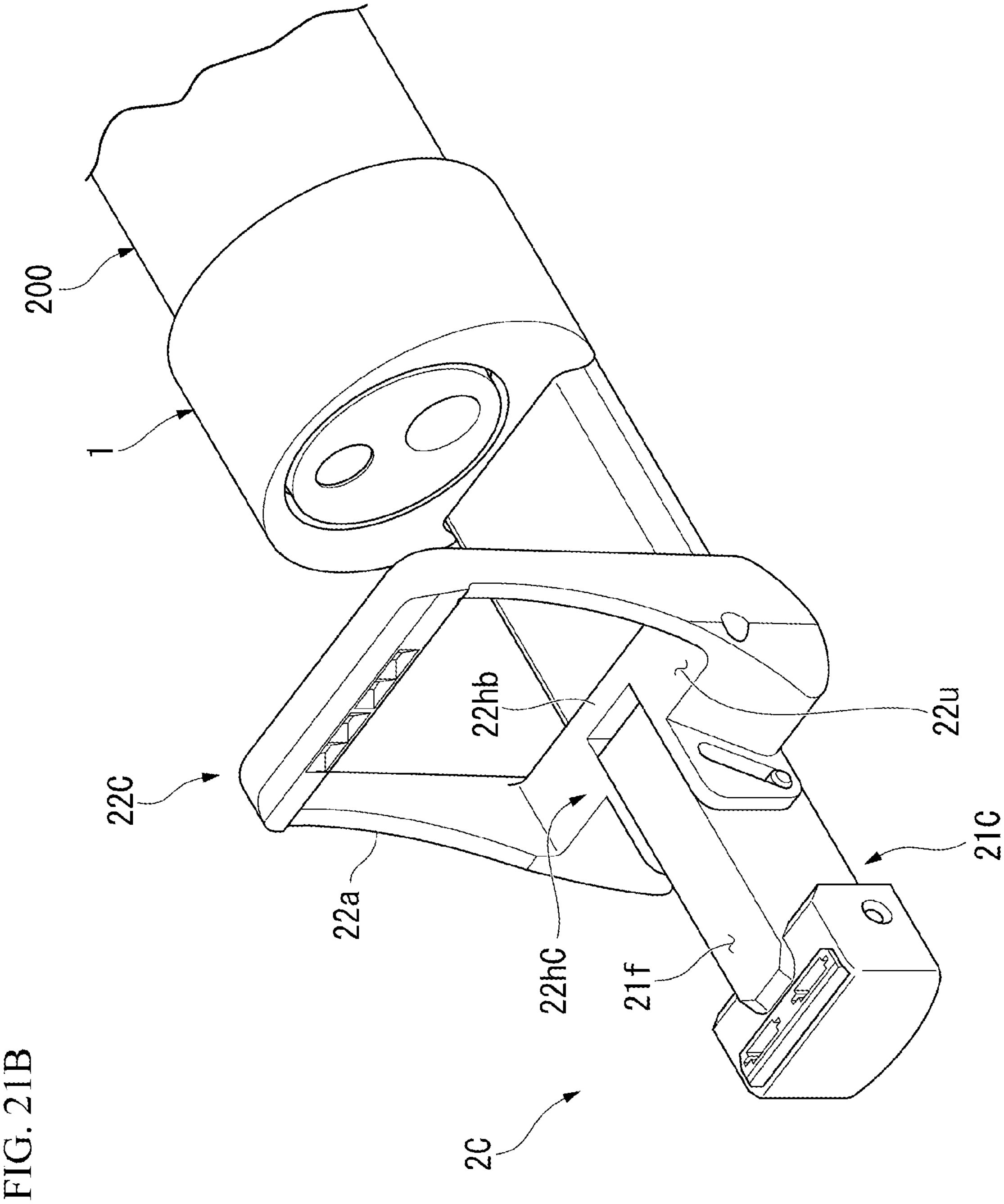
FIG. 21B is a perspective view showing the grasping portion in modified example 3.

FIGS. 21A and 21B are perspective views showing the grasping portion 2C in modified example 3.

Hereinafter, modified example 3 of the first embodiment will be described with reference to FIGS. 21A and 21B.

As shown in FIGS. 21A and 21B, the grasping portion 2C includes an anvil 22C including a third guide portion 22*h*C, and a stapling head 21C including a stepped portion 26 capable of accommodating the third guide portion 22*h*C.

The third guide portion 22*h*C formed on the anvil 22C side has a shape in which the pair of first guide portions 22*h*A in modified example 2 are connected and integrated. The third guide portion 22*h*C includes a pair of guide portions 22*h*A and a connecting portion 22*h*b that connects them. The connecting portion 22*h*b connects upper parts of the pair of guide portions 22*h*A facing each other via the stapling head 21. A groove portion 22*m* for preventing interference with the stapling head 21 is formed in a region surrounded by the pair of guide portions 22*h*A and the connecting portion 22*h*b. The groove portion 22*m* is formed in a dimension slightly larger than a thickness in a width direction of the stapling head 21.

The third guide portion 22*h*C includes a side surface 22*u* orthogonal to a length direction (axial direction A) of the anvil 22C and extending in the vertical direction B when the grasping portion 2C is in a closed state, and a third inclined surface 22*v* inclined from an upper end of the side surface 22*u* toward the downward side B2 toward a proximal-end side of the grasping portion 2C. The groove portion 22*m* opens at the side surface 22*u* and the third inclined surface 22*v*.

The stepped portion 26 formed on the stapling head 21C side is formed on a proximal-end side of the stapling head 21. The stepped portion 26 is formed throughout in the width direction of the stapling head 21. The stepped portion 26 can accommodate the entire connecting portion 22*h*b of the third guide portion 22*h*C when the anvil 22 is in an open state.

Further, the stepped portion 26 is not limited to being formed at the proximal end of the stapling head 21. For example, it may be formed in the middle of the stapling head 21 in a length direction. Also, a groove portion may be used instead of the stepped portion 26.

As shown in FIG. 21A, when the grasping portion 2C is in a closed state, the third guide portion 22*h*C of the anvil 22C protrudes to the upward side B1 of the stapling head 21C.

As shown in FIG. 21B, when the grasping portion 2C is in an open state, the third guide portion 22*h*C of the anvil 22C is in a retracted orientation, and the connecting portion 22*hb* thereof is accommodated in the stepped portion 26 of the stapling head 21C. In the third guide portion 22*h*C positioned in the retracted orientation, the side surface 22*u* thereof and an upper surface 21*f* of a first main body portion 21*b* of the stapling head 21C are substantially coplanar with each other.

According to the configuration of the modified example 3, when the grasping portion 2C is in a closed state, the third guide portion 22*h*C provided between second main body portions 22*b* on both left and right sides of the anvil 22C assumes a protruding orientation. When the third guide portion 22*h*C integrated throughout in the width direction of the anvil 22C is provided, the third guide portion 22*h*C also appears on the upward side B1 of the stapling head 21 when the grasping portion 2C is in a closed state. Therefore, since a groove or step is not formed in the width direction, the grasping forceps G can reliably ride on the third guide portion 22*h*C in the first advancing step S15 described above, and the grasping forceps G can be reliably lifted to the upward side B1 of the anvil 22C (second distal-end portion 22*c*).

Modified Example 4

For example, in the first embodiment, as shown in FIG. 10, the second distal-end portion 22*c* of the U-shaped member 22*a* of the anvil 22 in which the staple receiving portion 4 is provided has a substantially rectangular parallelepiped shape, but the present disclosure is not limited thereto.

An anvil 22D according to modified example 4 has a different cross-sectional shape on the second distal-end portion 22*c* side of U-shaped member 22*a*.

Figure 22:
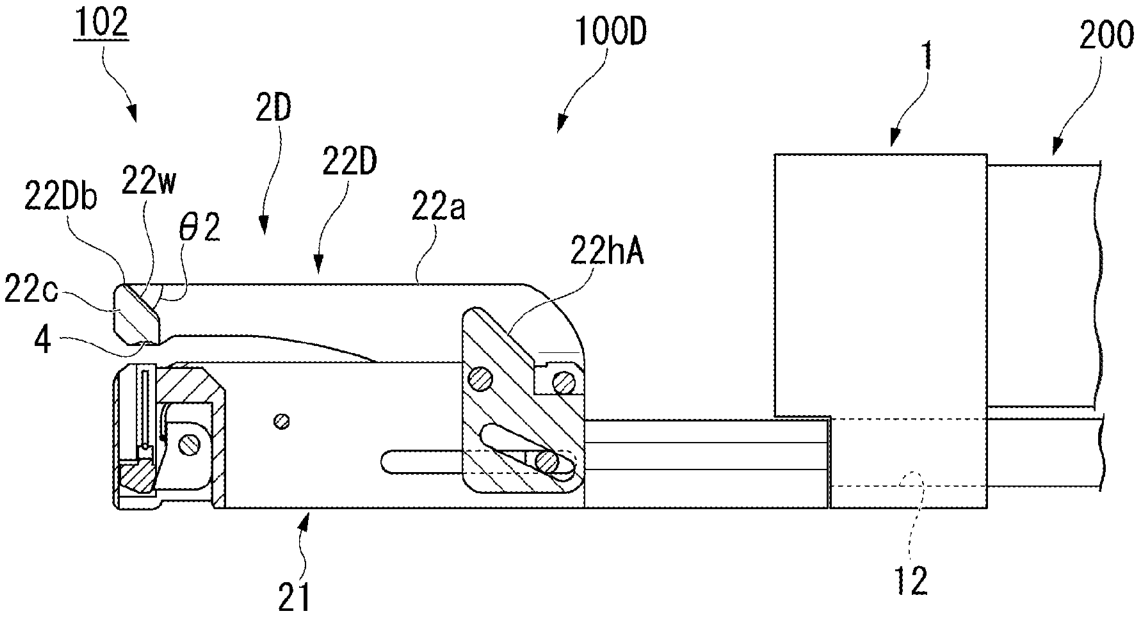
FIG. 22 is a cross-sectional view showing a grasping portion in modified example 4.

FIG. 22 is a cross-sectional view showing a grasping portion 2D in modified example 4.

Hereinafter, modified example 4 of the first embodiment will be described with reference to FIG. 22.

As shown in FIG. 22, the anvil 22D of the grasping portion 2D has an inclined surface 22*w* at the second distal-end portion 22*c* of the U-shaped member 22*a*. The inclined surface 22*w* is provided to be continuous with an outer surface 22Db of the anvil 22D on a side opposite to the staple receiving portion 4. When the grasping portion 2D is in a closed state, the inclined surface 22*w* is inclined from the outer surface 22Db toward the downward side B2 as it goes from the distal end to the proximal-end side. That is, the inclined surface 22*w* is inclined toward the first guide portion 22*h*A side that is positioned on the proximal-end side with respect to the inclined surface 22*w*.

The inclined surface 22*w* is preferably formed throughout in a width direction of the second distal-end portion 22*c* of the anvil 22, but the present disclosure is not limited thereto, and may be formed partially in the width direction of the second distal-end portion 22*c*. Also, an inclination angle θ2 of the inclined surface 22*w* with respect to a horizontal direction can be changed as appropriate.

According to the configuration of the modified example 4, when the inclined surface 22*w* is provided on a side opposite to the staple receiving portion 4 in the anvil 22D, when the grasping portion 2D is in a closed state, the operator advances the grasping forceps G that has been lifted by the first guide portion 22*h*A toward the distal-end side, and thereby the tissue V containing the treatment target T grasped by the grasping forceps G is made easier to ride on the inclined surface 22*w* of the anvil 22D. Therefore, turning up is easily achieved even with thick tissue V, and the operator can easily ascertain the suture position.

While the first embodiment and modified examples 1 to 4 of the present disclosure have been described in detail as above with reference to the drawings, the specific configurations are not limited to the embodiment and modified examples and may include design changes or the like within a range not departing from the gist of the present invention. Also, the components shown in the first embodiment and modified examples 1 to 4 described above can be configured by appropriately combining them.

Second Embodiment

Next, a medical stapler 102 of a second embodiment will be described with reference to FIG. 23. In the following description, components that are common to those already described will be denoted by the same reference signs and duplicate description will be omitted.

The medical stapler 102 according to the second embodiment has a different aspect of the anvil compared to the medical stapler 100 according to the first embodiment. In the first embodiment described above, as shown in FIGS. 6, 7, or the like, the visual space 25 surrounded by the U-shaped member 22*a* formed in a substantially U shape has been formed in the anvil 22, but an aspect of the anvil 22 is not limited thereto.

Figure 23:
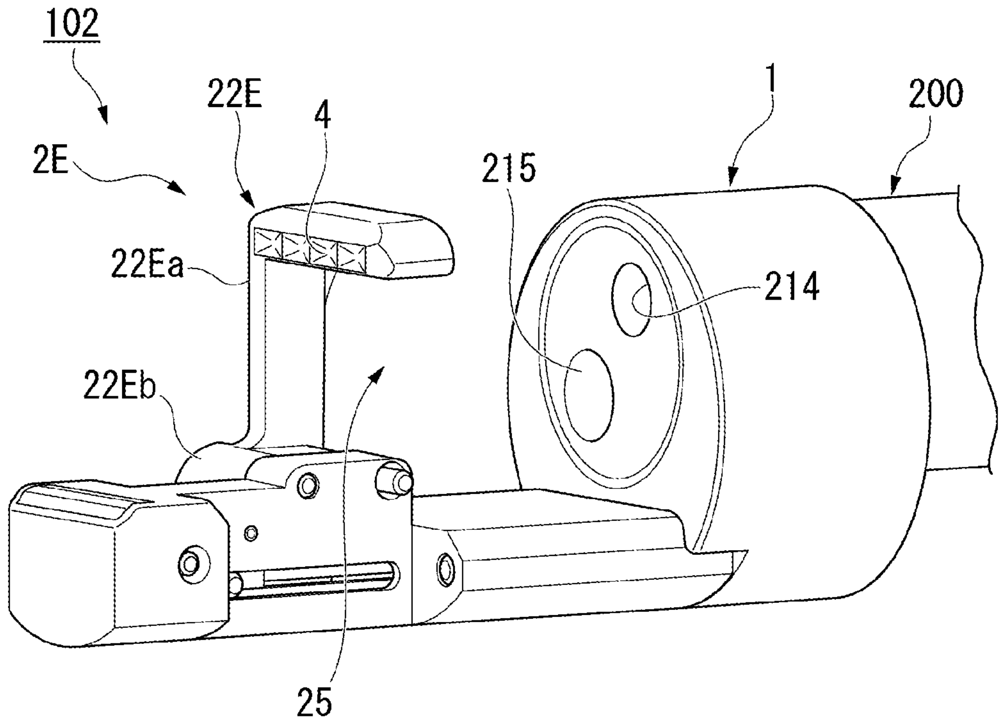
FIG. 23 is a perspective view showing a configuration of a medical stapler of a second embodiment.

FIG. 23 is a perspective view showing a configuration of the medical stapler 102 (grasping portion 2E) of the second embodiment.

The grasping portion 2E in the medical stapler 102 of the present embodiment includes an L-shaped member 22Ea formed in a substantially L shape, and a second main body portion 22Eb supporting the L-shaped member 22Ea to be rotatable. A staple receiving portion 4 is provided at a distal end of the L-shaped member 22Ea. A proximal end of the L-shaped member 22Ea is attached to the second main body portion 22Eb. In this case, a visual space 25 is a space sandwiched between sides of the L-shaped member 22Ea formed in a substantially L shape.

According to the medical stapler 102 of the second embodiment, as shown in FIG. 23, even when an anvil 22E is in an open state, the operator can observe a treatment target T via an imaging unit of an endoscope 200 and can treat the treatment target T by causing grasping forceps G to protrude from a forceps port 214.

While the second embodiment of the present disclosure has been described in detail with reference to the drawings, the specific configurations are not limited to the embodiment and may include design changes or the like within a range not departing from the gist of the present invention. Also, it is possible to configure the second embodiment by appropriately combining the components shown in the modified examples 1 to 4 of the first embodiment described above.

Third Embodiment

Next, a medical stapler 103 according to a third embodiment will be described with reference to FIGS. 24A and 24B. In the following description, components that are common to those already described will be denoted by the same reference signs and duplicate description will be omitted.

The medical stapler 103 according to the third embodiment differs from the medical staplers 100 and 102 according to the first and second embodiments in that a stapling head 21F varies. The first embodiment and second embodiment described above have had an aspect in which the stapling head 21 is fixed.

Figure 24A:
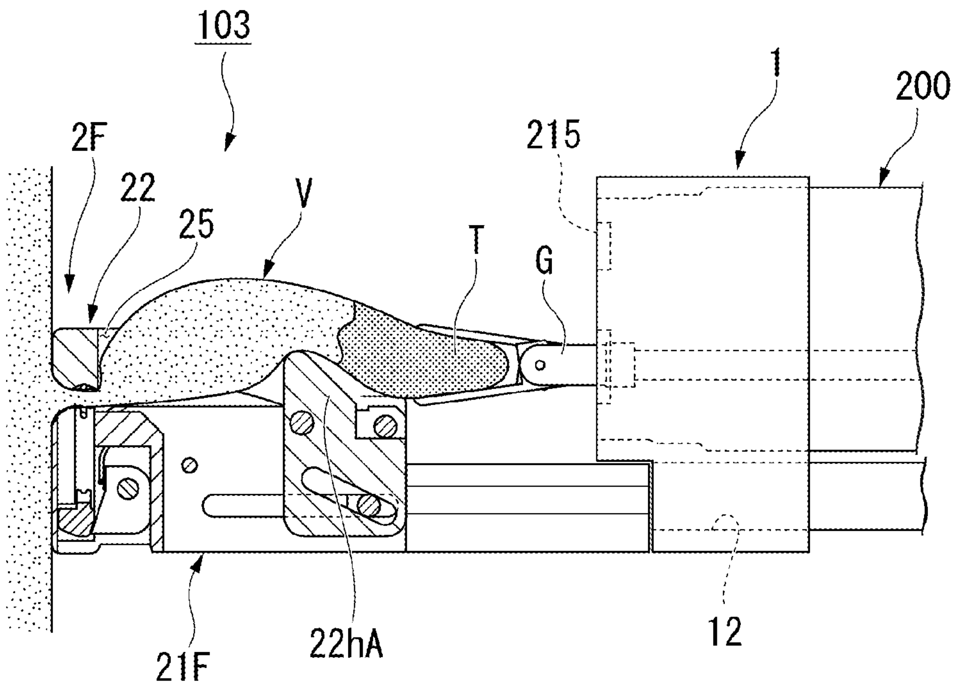
FIG. 24A is a cross-sectional view showing a configuration of a medical stapler of a third embodiment.
Figure 24B:
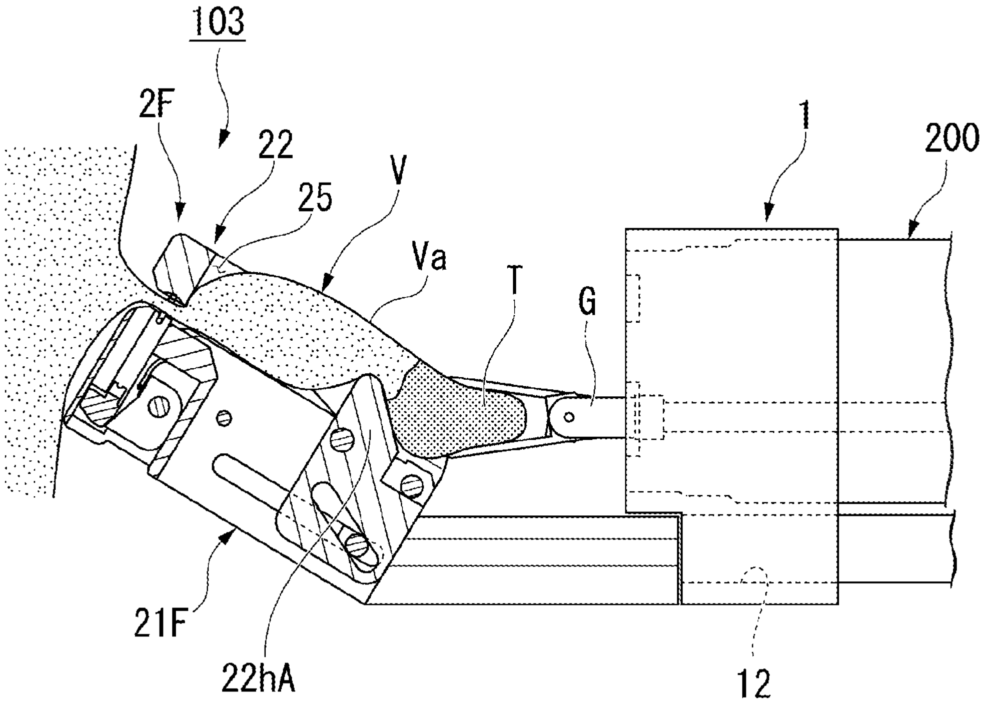
FIG. 24B is a cross-sectional view showing a configuration of the medical stapler of the third embodiment.

FIGS. 24A and 24B are cross-sectional views showing a configuration of the medical stapler 103 (grasping portion 2F) of the third embodiment.

The grasping portion 2F in the medical stapler 103 of the present embodiment has a configuration in which the stapling head 21F tilts with respect to an extended portion 24 provided on a proximal-end side of the stapling head 21F. As the stapling head 21F tilts, an anvil 22 coupled to the stapling head 21F also tilts at the same time. Regarding a tilting mechanism, it is possible to employ various existing technologies.

As shown in FIG. 24A, if a tissue V drawn into a visual space 25 by grasping forceps G is a thick tissue, since a surface Va of the tissue V tends to bulge, it is difficult to ascertain a suture site.

Therefore, as shown in FIG. 24B, when a distal-end side of the stapling head 21F is tilted in a state in which the tissue V drawn in by the grasping forceps G is sandwiched between the anvil 22 and the stapling head 21F, a grasped portion (suture position) can be ascertained from the surface Va side.

Thereafter, the grasped portion (suture position) may be ascertained from a back surface Vb side of the tissue V by advancing the grasping forceps G and lifting the grasping forceps G to the upward side B1 due to a first guide portion 22*h*A.

While the third embodiment of the present disclosure has been described in detail with reference to the drawings, the specific configurations are not limited to the embodiment and may include design changes or the like within a range not departing from the gist of the present invention. Also, it is possible to configure the third embodiment by appropriately combining the components shown in the first embodiment, modified examples 1 to 4, and the second embodiment described above.

Although the respective embodiments and modifications of the present disclosure have been described above, the technical scope of the present disclosure is not limited to the above-described embodiments, and configurations in the respective embodiments and modifications within the scope not departing from the spirit of the present disclosure. It is possible to change the combination of elements, make various changes to each configuration element, or delete each configuration element. For example, the configuration according to any one of above-described embodiments and modifications of the present disclosure may be appropriately combined with each modification of the operation section. The present disclosure is not limited by the above description, but only by the appended claims.

What is claimed is:

1. A medical stapler comprising:

a stapling head including a staple ejection portion, the stapling head having a length in one direction;

an anvil openably and closably coupled to the stapling head by a rotation shaft, the anvil having a length in one direction;

a staple receiving portion provided in the anvil, the staple receiving portion being provided at a position facing the staple ejection portion when the stapling head and the anvil are in a closed state; and a first guide portion configured to be displaced to a protruding orientation or a retracted orientation, wherein in the protruding orientation, the first guide portion protrudes in a direction in which the anvil opens with respect to the stapling head when the anvil is in a closed state with respect to the stapling head, in the retracted orientation, the first guide portion does not protrude in the direction in which the anvil opens with respect to the stapling head when the anvil is in an open state with respect to the stapling head, and in the protruding orientation, the first guide portion is capable of lifting a treatment tool.

2. The medical stapler according to claim 1, further comprising:

an endoscope; and an attachment member detachably attached to a distal-end portion of the endoscope, the attachment member having an opening through which an objective lens of the endoscope is exposed.

3. The medical stapler according to claim 1, wherein the anvil has a visual space passing through in an open-close direction between the stapling head and the rotation shaft, and the treatment tool is capable of passing through the visual space when the anvil is in the open state with respect to the stapling head.

4. The medical stapler according to claim 1, wherein the first guide portion is provided in the anvil.

5. The medical stapler according to claim 1, wherein the first guide portion is provided on a path of the treatment tool.

6. The medical stapler according to claim 1, wherein the first guide portion is disposed on both sides of the stapling head in a width direction intersecting a length direction.

7. The medical stapler according to claim 6, wherein the first guide portions are coupled to each other via the stapling head.

8. The medical stapler according to claim 1, wherein the first guide portion has a first inclined surface, and the first inclined surface is inclined in a direction away from the stapling head from a proximal-end side of the anvil toward a distal-end side of the anvil when the anvil is in the closed state with respect to the stapling head.

9. The medical stapler according to claim 1, wherein the stapling head includes a second guide portion protruding in a direction in which the anvil opens with respect to the staple ejection portion.

10. The medical stapler according to claim 9, wherein the second guide portion includes a second inclined surface, and the second inclined surface is inclined to protrude in a direction in which the anvil opens from an endoscope side toward a distal-end side of the stapling head.

11. The medical stapler according to claim 9, wherein the second guide portion is disposed at a position adjacent to the first guide portion.

12. A suturing method comprising:

an insertion step of inserting a medical stapler and an endoscope into a body;

a grasping step of grasping a treatment target inside the body with a treatment tool;

a retracting step of retracting the treatment tool relative to the medical stapler to draw in the treatment target to an endoscope side;

a suturing step of ejecting a staple from a stapling head of the medical stapler to suture a circumference of the treatment target;

a first advancing step of advancing the treatment tool with respect to the medical stapler by causing the treatment tool to protrude from the endoscope;

a first open-close step of bringing an anvil into an open state with respect to the stapling head at a portion close to the treatment target to place a first guide portion in a retracted orientation;

a retracting step of retracting the treatment tool relative to the medical stapler to draw in the treatment target to the endoscope side through a visual space;

a second open-close step of bringing the anvil into a closed state with respect to the stapling head to place the first guide portion in a protruding orientation; and a second advancing step of advancing the treatment tool until the treatment tool rides on the first guide portion.

13. The suturing method according to claim 12, wherein in the retracting step, the treatment tool retracts relative to the medical stapler to draw in the treatment target to the endoscope side with respect to the first guide portion through the visual space.

14. The suturing method according to claim 12, wherein in the second advancing step, the treatment tool advances toward a distal-end portion side of the anvil to lift the treatment target on the distal-end portion.

15. The suturing method according to claim 12, further comprising:

an observation step of projecting, on a display device, the treatment target within a field of view showing a distal-end portion of the endoscope.

16. A suturing method comprising:

an insertion step of inserting a medical stapler and an endoscope into a body, wherein the medical stapler includes:

a stapling head including a staple ejection portion, the stapling head having a length in one direction;

an anvil openably and closably coupled to the stapling head by a rotation shaft, the anvil having a length in one direction;

a staple receiving portion provided in the anvil, the staple receiving portion being provided at a position facing the staple ejection portion when the stapling head and the anvil are in a closed state; and a first guide portion configured to be displaced to a protruding orientation or a retracted orientation, wherein in the protruding orientation, the first guide portion protrudes in a direction in which the anvil opens with respect to the stapling head when the anvil is in a closed state with respect to the stapling head, in the retracted orientation, the first guide portion does not protrude in the direction in which the anvil opens with respect to the stapling head when the anvil is in an open state with respect to the stapling head, and in the protruding orientation, the first guide portion is capable of lifting a treatment tool;

a grasping step of grasping a treatment target inside the body with a treatment tool;

a retracting step of retracting the treatment tool relative to the medical stapler to draw in the treatment target to an endoscope side; and a suturing step of ejecting a staple from a stapling head of the medical stapler to suture a circumference of the treatment target, wherein in the suturing step, a plurality of staples are ejected from the stapling head.

17. The suturing method according to claim 16, further comprising:

an observation step of projecting, on a display device, the treatment target within a field of view showing a distal-end portion of the endoscope.

* * * * *